United States Patent
Ross et al.

[11] Patent Number: 5,945,557
[45] Date of Patent: Aug. 31, 1999

[54] BENZYLOXY SUBSTITUTED AROMATICS AND THEIR USE AS FUNGICIDES AND INSECTICIDES

[75] Inventors: Ronald Ross, Jamison; Ted Tsutomu Fujimoto, Churchville; Steven Howard Shaber, Horsham, all of Pa.

[73] Assignee: Rohm and Haas Company, Philadelphia, Pa.

[21] Appl. No.: 09/102,713

[22] Filed: Jun. 23, 1998

Related U.S. Application Data

[60] Provisional application No. 60/051,683, Jul. 3, 1997.

[51] Int. Cl.$^6$ .......................... C07C 69/76; C07C 233/00
[52] U.S. Cl. .................... 560/52; 560/55; 560/60; 564/169; 564/171
[58] Field of Search ................ 560/52, 55, 60; 564/169, 171

[56] References Cited

U.S. PATENT DOCUMENTS

| | | |
|---|---|---|
| 4,914,128 | 4/1990 | Schirmer et al. |
| 4,999,042 | 3/1991 | Anthony et al. |
| 5,075,471 | 12/1991 | Michelotti et al. |
| 5,145,980 | 9/1992 | Wenderoth et al. |
| 5,157,144 | 10/1992 | Anthony et al. |
| 5,185,342 | 2/1993 | Hayase et al. |
| 5,221,691 | 6/1993 | Clough et al. |
| 5,252,594 | 10/1993 | Shaber et al. |
| 5,387,714 | 2/1995 | Takase et al. |
| 5,407,902 | 4/1995 | Oda et al. |
| 5,430,172 | 7/1995 | Grammenos et al. |
| 5,523,454 | 6/1996 | Brand et al. |

FOREIGN PATENT DOCUMENTS

| | | |
|---|---|---|
| 0 477 631 A1 | 4/1992 | European Pat. Off. |
| 43 12 637 A 1 | 10/1994 | Germany |
| 4312637 | 10/1994 | Germany |

*Primary Examiner*—Paul J. Killos
*Attorney, Agent, or Firm*—Guy T. Donatiello

[57] ABSTRACT

Compounds with fungicidal and insecticidal properties having formula

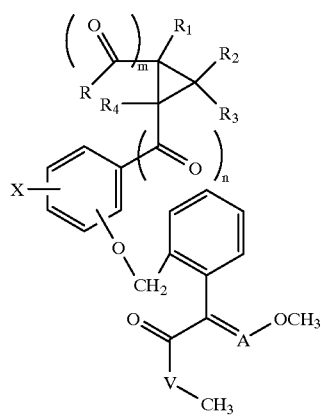

wherein A is N or CH; V is O or NH;

m and n are the integers 0 and 1, provided that m+n is 0 or 1;

X is independently selected from hydrogen, halo, $(C_1-C_4)$ alkyl, and $(C_1-C_4)$ alkoxy;

R is independently selected from hydrogen, $(C_1-C_{12})$ alkyl, $(C_1-C_{12})$ alkoxy, halo$(C_1-C_{12})$ alkyl, $(C_2-C_{12})$ alkenyl, $(C_2-C_{12})$ alkynyl, $(C_1-C_{12})$ alkoxy$(C_1-C_{12})$ alkyl, $(C_3-C_7)$ cycloalkyl, halo$(C_3-C_7)$ cycloalkyl, $(C_3-C_7)$ cycloalkyl $(C_1-C_{12})$ alkyl, $(C_3-C_7)$ cycloalkyl $(C_2-C_{12})$ alkenyl, $(C_3-C_7)$ cycloalkyl $(C_2-C_{12})$ alkynyl, $(C_1-C_{12})$ alkyl $(C_3-C_7)$ cycloalkyl, $(C_1-C_{12})$ alkoxy $(C_3-C_7)$ cycloalkyl, $(C_1-C_{12})$ alkoxy $(C_1-C_{12})$ alkyl$(C_3-C_7)$ cycloalkyl, $(C_2-C_{12})$ alkenyl $(C_3-C_7)$ cycloalkyl, $(C_2-C_{12})$ alkynyl $(C_3-C_7)$ cycloalkyl, halo$(C_1-C_{12})$ alkyl $(C_3-C_7)$ cycloalkyl, $(C_1-C_{12})$ alkoxy $(C_2-C_{12})$ alkenyl$(C_3-C_7)$ cycloalkyl, $(C_1-C_{12})$ alkoxy $(C_2-C_{12})$ alkynyl$(C_3-C_7)$ cycloalkyl, $(C_3-C_7)$ cycloalkyl $(C_3-C_7)$ cycloalkyl, $(C_1-C_{12})$ alkyl $(C_3-C_7)$ cycloalkyl$(C_3-C_7)$ cycloalkyl, $(C_2-C_{12})$ alkenyl $(C_3-C_7)$ cycloalkyl$(C_3-C_7)$ cycloalkyl, $(C_2-C_{12})$ alkynyl $(C_3-C_7)$ cycloalkyl$(C_3-C_7)$ cycloalkyl, $(C_3-C_7)$ cycloalkyl $(C_1-C_{12})$ alkyl$(C_3-C_7)$ cycloalkyl, $(C_3-C_7)$ cycloalkyl $(C_2-C_{12})$ alkenyl$(C_3-C_7)$ cycloalkyl, $(C_3-C_7)$ cycloalkyl $(C_2-C_{12})$ alkynyl$(C_3-C_7)$ cycloalkyl, $(C_3-C_7)$ cycloalkyl $(C_1-C_{12})$ alkoxy$(C_3-C_7)$ cycloalkyl, $(C_1-C_{12})$ alkoxy$(C_1-C_{12})$ alkyl$(C_3-C_7)$ cycloalkyl, $(C_3-C_7)$ cycloalkyl$(C_1-C_{12})$ alkoxy$(C_1-C_{12})$ alkenyl$(C_3-C_7)$ cycloalkyl, $(C_3-C_7)$ cycloalkyl$(C_1-C_{12})$ alkoxy$(C_1-C_{12})$ alkynyl$(C_3-C_7)$ cycloalkyl, aryl, aralkyl, aryl$(C_3-C_7)$ cycloalkyl, aryl$(C_3-C_7)$ cycloalkyl$(C_3-C_7)$ cycloalkyl, $(C_3-C_7)$ cycloalkylaryl, aryl$(C_1-C_4)$ alkyl$(C_3-C_7)$ cycloalkyl, heterocyclic, aryl$(C_1-C_4)$ alkylheterocyclic heterocyclic$(C_1-C_4)$ alkyl, heterocyclic$(C_3-C_7)$ cycloalkyl and $R_1$, $R_2$, $R_3$ and $R_4$ are independently selected from hydrogen, halogen, $(C_1-C_{12})$ alkyl, $(C_1-C_{12})$ alkoxy, halo$(C_1-C_{12})$ alkyl, $(C_2-C_{12})$ alkenyl, $(C_2-C_{12})$ alkynyl, $(C_3-C_7)$ cycloalkyl, cyano, carboxy, $(C_1-C_4)$ alkoxycarbonyl, aryl, and when taken together $R_2$ and $R_3$ form a $(C_3-C_7)$ cycloalkyl ring, provided that when n=0 or 1 and m=0 R and $R_1$ are not both hydrogen and when A is N and V is NH and n and m are both zero than R, $R_1$, $R_2$, $R_3$ and $R_4$ are other than 1 to 3 substituents independently selected from halogen and $(C_1-C_4)$alkyl.

16 Claims, No Drawings

BENZYLOXY SUBSTITUTED AROMATICS AND THEIR USE AS FUNGICIDES AND INSECTICIDES

This application claims benefit of Provisional Application 60/051,683, filed Jul. 3, 1997.

The present invention relates to benzyloxy substituted phenyl compounds, compositions containing these compounds and methods for controlling fungi and insects by the use of a fungitoxic or insecticidal amount of these compounds.

It is known that propenoic acids and oxime ethers of certain benzyloxy substituted phenyl compounds are useful as fungicides. The substitution of the phenyl ring by cycloalkyl is known in the art (see for example U.S. Pat. No. 5,145,980).

We have discovered phenyl derivatives which possess a substituted cyclopropyl moiety. These novel derivatives also possess fungicidal and insecticidal properties.

The novel benzyloxy substituted phenyl compounds of the present invention have the Formula (I)

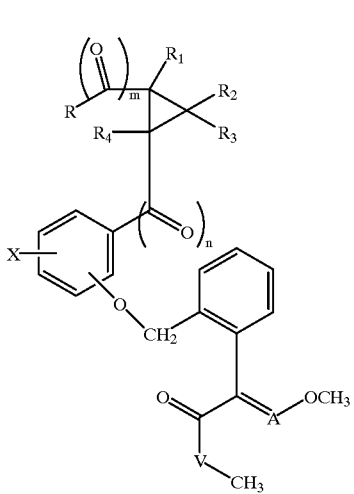

its enantiomers and stereoisomers and agronomically acceptable salts, wherein A is N or CH; V is O or NH;

m and n are the integers 0 and 1, provided that m+n is 0 or 1;

X is independently selected from hydrogen, halo, $(C_1-C_4)$alkyl, and $(C_1-C_4)$alkoxy;

R is selected from hydrogen, $(C_1-C_{12})$alkyl, $(C_1-C_{12})$alkoxy, halo$(C_1-C_{12})$alkyl, $(C_2-C_{12})$alkenyl, $(C_2-C_{12})$alkynyl, $(C_1-C_{12})$alkoxy$(C_1-C_{12})$alkyl, $(C_3-C_7)$cycloalkyl, halo$(C_3-C_7)$cycloalkyl, $(C_3-C_7)$cycloalkyl$(C_1-C_{12})$alkyl, $(C_3-C_7)$cycloalkyl$(C_2-C_{12})$alkenyl, $(C_3-C_7)$cycloalkyl$(C_2-C_{12})$alkynyl, $(C_1-C_{12})$alkyl$(C_3-C_7)$cycloalkyl, $(C_1-C_{12})$alkoxy$(C_3-C_7)$cycloalkyl, $(C_1-C_{12})$alkoxy$(C_1-C_{12})$alkyl$(C_3-C_7)$cycloalkyl, $(C_2-C_{12})$alkenyl$(C_3-C_7)$cycloalkyl, $(C_2-C_{12})$alkynyl$(C_3-C_7)$cycloalkyl, halo$(C_1-C_{12})$alkyl$(C_3-C_7)$cycloalkyl, $(C_1-C_{12})$alkoxy$(C_2-C_{12})$alkenyl$(C_3-C_7)$cycloalkyl, $(C_1-C_{12})$alkoxy$(C_2-C_{12})$alkynyl$(C_3-C_7)$cycloalkyl, $(C_3-C_7)$cycloalkyl$(C_3-C_7)$cycloalkyl, $(C_1-C_{12})$alkyl$(C_3-C_7)$cycloalkyl$(C_3-C_7)$cycloalkyl, $(C_2-C_{12})$alkenyl$(C_3-C_7)$cycloalkyl$(C_3-C_7)$cycloalkyl, $(C_2-C_{12})$alkynyl$(C_3-C_7)$cycloalkyl$(C_3-C_7)$cycloalkyl, $(C_3-C_7)$cycloalkyl$(C_1-C_{12})$alkyl$(C_3-C_7)$cycloalkyl, $(C_3-C_7)$cycloalkyl$(C_2-C_{12})$alkenyl$(C_3-C_7)$cycloalkyl, $(C_3-C_7)$cycloalkyl$(C_2-C_{12})$alkynyl$(C_3-C_7)$cycloalkyl, $(C_3-C_7)$cycloalkyl$(C_1-C_{12})$alkoxy$(C_3-C_7)$cycloalkyl, $(C_3-C_7)$cycloalkyl$(C_1-C_{12})$alkoxy$(C_1-C_{12})$alkyl$(C_3-C_7)$cycloalkyl, $(C_3-C_7)$cycloalkyl$(C_1-C_{12})$alkoxy $(C_1-C_{12})$alkenyl$(C_3-C_7)$cycloalkyl, $(C_3-C_7)$cycloalkyl $(C_1-C_{12})$alkoxy$(C_1-C_{12})$alkynyl$(C_3-C_7)$cycloalkyl, aryl, aralkyl, aryl$(C_3-C_7)$cycloalkyl, aryl$(C_3-C_7)$cycloalkyl $(C_3-C_7)$cycloalkyl, $(C_3-C_7)$cycloalkylaryl, aryl$(C_1-C_4)$alkyl$(C_3-C_7)$cycloalkyl, heterocyclic, aryl$(C_1-C_4)$alkylheterocyclic heterocyclic$(C_1-C_4)$alkyl, heterocyclic $(C_3-C_7)$cycloalkyl and $R_1$, $R_2$, $R_3$ and $R_4$ are independently selected from hydrogen, halogen, $(C_1-C_{12})$alkyl, $(C_1-C_{12})$alkoxy, halo $(C_1-C_{12})$alkyl, $(C_2-C_{12})$alkenyl, $(C_2-C_{12})$alkynyl, $(C_3-C_7)$cycloalkyl, cyano, carboxy, $(C_1-C_4)$alkoxycarbonyl, aryl, and when taken together $R_2$ and $R_3$ form a $(C_3-C_7)$cycloalkyl ring, provided that when n=0 or 1 and m=0 then R and $R_1$ are not both hydrogen and when A is N and V is NH and n and m are both zero then R, $R_1$, $R_2$, $R_3$ and $R_4$ are other than 1 to 3 substituents independently selected from halogen and $(C_1-C_4)$alkyl.

The aforementioned $(C_1-C_{12})$alkyl, $(C_1-C_{12})$alkoxy, $(C_2-C_{12})$alkenyl, $(C_2-C_{12})$alkynyl and $(C_3-C_7)$cycloalkyl groups may be optionally substituted with up to three substituents selected from the group consisting of halogen, nitro, trihalomethyl and cyano.

The term alkyl includes both branched and straight chain alkyl groups from 1 to 12 carbon atoms. Typical alkyl groups are methyl, ethyl, n-propyl, iso-propyl, n-butyl, sec-butyl, isobutyl,t-butyl, n-pentyl, isopentyl, n-hexyl, n-heptyl, isooctyl, nonyl, decyl, undecyl, dodecyl and the like. The term haloalkyl refers to an alkyl group substituted with 1 to 3 halogens.

The term alkenyl refers to an ethylenically unsaturated hydrocarbon group, straight or branched, having a chain length of 2 to 12 carbon atoms and 1 or 2 ethylenic bonds. The term haloalkenyl refers to an alkenyl group substitued with 1 to 3 halogen atoms. The term alkynyl refers to an unsaturated hydrocarbon group, straight or branched, having a chain length of 2 to 12 carbon atoms and 1 or 2 acetylenic bonds.

The term cycloalkyl refers to a saturated ring system having 3 to 7 carbon atoms.

The term aryl includes phenyl or napthyl, which maybe substituted with up to three substituents independently selected from the group consisting of halogen, cyano, nitro, trihalomethyl, phenyl, phenoxy, $(C_1-C_6)$alkyl, $(C_1-C_4)$alkylthio, $(C_1-C_4)$alkylsulfoxide, $(C_1-C_6)$alkoxy and halo $(C_1-C_4)$alkyl.

Typical aryl substituents include but are not limited to 4-chlorophenyl, 4-fluorophenyl, 4-bromophenyl, 2-methoxyphenyl, 2-methylphenyl, 3-methyphenyl, 4-methylphenyl, 2,4-dibromophenyl, 3,5-difluorophenyl, 2,4,6-trichlorophenyl, 4-methoxyphenyl, 2-chloronapthyl, 2,4-dimethoxyphenyl, 4-(trifluoromethyl)phenyl and 2-iodo-4-methylphenyl.

The term heterocyclic refers to a substituted or unsubstituted 5 or 6 membered unsaturated ring containing one, two or three heteroatoms, preferably one or two heteroatoms independently selected from oxygen, nitrogen and sulfur or to a bicyclic unsaturated ring system containing up to 10 atoms including one heteroatom selected from oxygen, nitrogen and sulfur. Examples of heterocycles include but are not limited to 2-, 3- or 4-pyridinyl, pyrazinyl, 2-, 4-, or 5-pyrimidinyl, pyridazinyl, triazolyl, imidazolyl, 2- or 3-thienyl, 2- or 3-furyl, pyrrolyl, oxazolyl, isoxazolyl, thiazolyl, isothiazolyl, oxadiazolyl, thiadiazolyl, quinolyl and isoquinolyl. The heterocyclic ring may be optionally substituted with up to two substituents independently selected from ($C_1$–$C_2$) alkyl, halogen, cyano, nitro and trihalomethyl.

The term aralkyl is used to describe a group wherein the alkyl chain is from 1 to 10 carbon atoms and can be branched or straight chain, preferably a straight chain, with the aryl portion, as defined above, forming a terminal portion of the aralkyl moiety. Typical aralkyl moieties are optionally substituted benzyl, phenethyl, phenpropyl and phenbutyl moieties. Typical benzyl moieties are 2-chlorobenzyl, 3-chlorobenzyl, 4-chlorobenzyl, 2-fluorobenzyl, 3-fluorobenzyl, 4-fluorobenzyl, 4-trifluoromethylbenzyl, 2,4-dichlorobenzyl, 2,4-dibromobenzyl, 2-methylbenzyl, 3-methylbenzyl, and 4-methylbenzyl. Typical phenethyl moieties are 2-(2-chlorophenyl)ethyl, 2-(3-chlorophenyl)ethyl, 2-(4-chlorophenyl)ethyl, 2-(2-fluorophenyl)ethyl, 2-(3-fluorophenyl)ethyl, 2-(4-fluorophenyl)ethyl, 2-(2-methylphenyl)ethyl, 2-(3-methyl-phenyl)ethyl, 2-(4-methylphenyl)ethyl, 2-(4-trifluoromethylphenyl)ethyl, 2-(2-methoxy-phenyl)ethyl, 2-(3-methoxyphenyl)ethyl, 2-(4-methoxyphenyl)ethyl, 2-(2,4-dichlorophenyl)-ethyl, 2-(3,5-dimethoxyphenyl)ethyl. Typical phenpropyl moieties are 3-phenylpropyl, 3-(2-chlorophenyl)propyl, 3-(3-chlorophenyl)propyl, 3-(4-chlorophenyl)propyl, 3-(2,4-dichloro-phenyl)propyl, 3-(2-fluorophenyl)propyl, 3-(3-fluorophenyl)propyl, 3-(4-fluorophenyl)propyl, 3-(2-methylphenyl)propyl, 3-(3-methylphenyl)propyl, 3-(4-methylphenyl)ethyl, 3-(2-methoxy-phenyl)propyl, 3-(3-methoxyphenyl)propyl, 3-(4-methoxyphenyl)propyl, 3-(4-trifluoromethylphenyl)propyl, 3-(2,4-dichlorophenyl)propyl and 3-(3,5-dimethoxyphenyl)propyl. Typical phenbutyl moities include are 4-phenylbutyl, 4-(2-chlorophenyl)butyl, 4-(3-chlorophenyl)butyl, 4-(4-chlorophenyl)butyl, 4-(2-fluorophenyl)butyl, 4-(3-fluorophenyl)butyl, 4-(4-fluorophenyl)-butyl, 4-(2-methylphenyl)butyl, 4-(3-methylphenyl)butyl, 4-(4-methylphenyl)butyl, 4-(2,4-dichlorophenyl)butyl, 4-(2-methoxphenyl)butyl, 4-(3-methoxyphenyl)butyl and 4-(4-methoxyphenyl)butyl.

Halogen or halo is meant to include iodo, fluoro, bromo and chloro moieties.

Because of the C=N double bonds, the novel compounds of the general Formula I may be obtained in preparation as E/Z isomeric mixtures. These isomers can be separated into individual components by conventional means. The cyclopropanes of Formula I may be obtained in preparation as cis and trans isomeric mixtures which can be separated into individual components by conventional means. Both the individual isomeric compounds and mixtures thereof form subjects of the invention and can be used as fungicides.

A preferred embodiment of this invention are the compounds, enantiomorphs and salts of Formula (I) where X is hydrogen and R is ($C_1$–$C_{12}$)alkyl, ($C_2$–$C_{12}$)alkenyl, ($C_2$–$C_{12}$)alkynyl, ($C_3$–$C_7$)cycloalkyl, ($C_3$–$C_7$)cycloalkyl($C_1$–$C_{12}$)alkyl, ($C_3$–$C_7$)cycloalkyl($C_2$–$C_{12}$)alkenyl, ($C_1$–$C_{12}$)alkyl($C_3$–$C_7$)cycloalkyl, ($C_2$–$C_{12}$)alkenyl($C_3$–$C_7$)cycloalkyl, phenyl substituted with preferably one or two substituents independently selected from halo, trihalomethyl, cyano, ($C_1$–$C_4$)alkyl, ($C_1$–$C_4$)alkylthio, ($C_1$–$C_4$)alkoxy or phenyl, where the $OCH_2$(2-substitutedphenyl) is bonded at the meta position to the $(CO)_n$cyclopropyl ring substituent of the phenyl ring as shown in Formula I'.

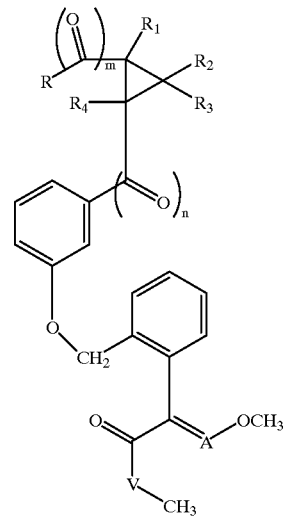

I'

A more preferred embodiment of this invention are the compounds, enantiomorphs, salts and complexes of Formula (I') where n is zero, m is zero or 1, R is ($C_3$–$C_7$)cycloalkyl, phenyl substituted with preferably one or two substituents independently selected from halo or trihalomethyl, $R_1$, $R_2$, $R_3$ and $R_4$ are hydrogen and A is N and V is NH. The preferred geometry when A is N is the E isomer as shown in Formula I"

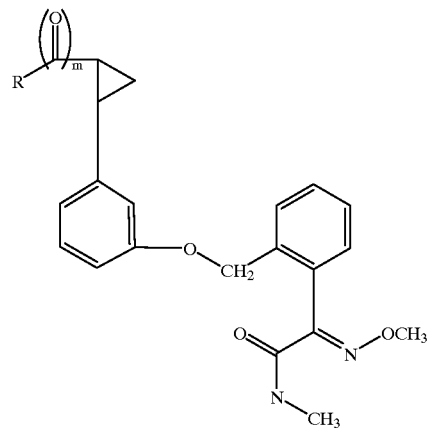

I"

Typical compounds encompassed by the present invention of Formula I include those compounds presented in Table I of Formula II, III and IV where X=H and $R_1$=$R_2$=$R_3$=$R_4$=H and n and m are zero.

II

[Structure II: cyclopropyl-R attached to meta position of phenyl, linked via OCH₂ to phenyl bearing C(=A-OCH₃)C(=O)V-CH₃]

III

[Structure III: cyclopropyl-R attached to ortho position of phenyl, linked via OCH₂ to phenyl bearing C(=A-OCH₃)C(=O)V-CH₃]

IV

[Structure IV: cyclopropyl-R attached to para position of phenyl, linked via OCH₂ to phenyl bearing C(=A-OCH₃)C(=O)V-CH₃]

TABLE 1

| Cmpd# | R | Formula | A | V |
|---|---|---|---|---|
| 1.01 | Ar | II | CH | O |
| 1.02 | Ar | III | CH | O |
| 1.03 | Ar | IV | CH | O |
| 1.04 | 4-Cl(Ar) | II | CH | O |
| 1.05 | 4-Cl(Ar) | III | CH | O |
| 1.06 | 4-Cl(Ar) | IV | CH | O |
| 1.07 | 2-Cl(Ar) | II | CH | O |
| 1.08 | 3-Cl(Ar) | III | CH | O |
| 1.09 | 2-F(Ar) | II | CH | O |
| 1.10 | 4-F(Ar) | II | CH | O |

TABLE 1-continued

| Cmpd# | R | Formula | A | V |
|---|---|---|---|---|
| 1.11 | 2-CH3(Ar) | II | CH | O |
| 1.12 | 3-CH3(Ar) | II | CH | O |
| 1.13 | 4-CH₃(Ar) | II | CH | O |
| 1.14 | 4-CH₃O(Ar) | II | CH | O |
| 1.15 | 2-CH₃O(Ar) | II | CH | O |
| 1.16 | 2,5-Cl(Ar) | II | CH | O |
| 1.17 | 3,4-Cl(Ar) | II | CH | O |
| 1.18 | CH₃ | II | CH | O |
| 1.19 | CH₃CH₂ | II | CH | O |
| 1.20 | CH₃CH₂CH₂ | II | CH | O |
| 1.21 | (CH₃)₂CH | II | CH | O |
| 1.22 | CH₃(CH₂)₂CH₂ | II | CH | O |
| 1.23 | CH₃(CH₂)₄CH₂ | II | CH | O |
| 1.24 | (CH₃)₂CHCH₂ | II | CH | O |
| 1.25 | CH₃CH₂(CH₃)CH | II | CH | O |
| 1.26 | (CH₃)₃C | II | CH | O |
| 1.27 | (CH₃)CHCH₂CH₂ | II | CH | O |
| 1.28 | CH₃CH₂CH₂(CH₃)CH | II | CH | O |
| 1.29 | CH₃CH₂(CH3)₂C | II | CH | O |
| 1.30 | CF₃ | II | CH | O |
| 1.31 | CF₃CF₂ | II | CH | O |
| 1.32 | CF₃CH₂ | II | CH | O |
| 1.33 | CH₂=CH | II | CH | O |
| 1.34 | cyclopropyl | II | CH | O |
| 1.35 | cyclopentyl | II | CH | O |
| 1.36 | cyclohexyl | II | CH | O |
| 1.37 | CH₂=C(cyclopropyl) | II | CH | O |
| 1.38 | CH₃—CH=C(cyclopropyl) | II | CH | O |
| 1.39 | CH₃O—CH=C(cyclopropyl) | II | CH | O |
| 1.40 | C₂H₅—CH=C(cyclopropyl) | II | CH | O |
| 1.41 | CH₂=C(CH(CH₃)₂ | II | CH | O |
| 1.42 | CH₃CH=C(CH(CH₃)₂ | II | CH | O |
| 1.43 | pyridin-3-yl | II | CH | O |
| 1.44 | pyrimidin-2-yl | II | CH | O |
| 1.45 | thien-2-yl | II | CH | O |
| 1.46 | thien-3-yl | II | CH | O |
| 1.47 | 2-napthyl | II | CH | O |
| 1.48 | 2-furyl | II | CH | O |
| 1.49 | 3-furyl | II | CH | O |
| 1.50 | 2-methylcyclopropyl | II | CH | O |
| 1.51 | 2-ethylcyclopropyl | II | CH | O |
| 1.52 | 2-(n-propyl)cyclopropyl | II | CH | O |
| 1.53 | 2-(n-butyl)cyclopropyl | II | CH | O |
| 1.54 | 2-(iso-butyl)cyclopropyl | II | CH | O |
| 1.55 | 2-(sec-butyl)cyclopropyl | II | CH | O |
| 1.56 | 2-(n-pentyl)cyclopropyl | II | CH | O |
| 1.57 | 2-(iso-pentyl)cyclopropyl | II | CH | O |
| 1.58 | 2-(n-hexyl)cyclopropyl | II | CH | O |
| 1.59 | 2-methoxycyclopropyl | II | CH | O |
| 1.60 | 2-(CH₃O)cyclopropyl | II | CH | O |
| 1.61 | 2-(CH₃CH₂O)cyclopropyl | II | CH | O |
| 1.62 | 1-methylcyclopropyl | II | CH | O |
| 1.63 | 2-(CH₂=CH₂)cyclopropyl | II | CH | O |
| 1.64 | 2-(l-cyclopropyl)cyclopropyl | II | CH | O |
| 1.65 | 2-(2-cyclopropyl)cyclopropyl | II | CH | O |
| 1.66 | cyclopropyl-CH₂ | II | CH | O |
| 1.67 | cyclopropyl-CH=CH | II | CH | O |
| 1.68 | 2-((2'-CH₃)cyclopropyl)cyclopropyl | II | CH | O |
| 1.69 | 2-(2'-CH₂=CH₂)cyclopropylcyclopropyl | II | CH | O |
| 1.70 | 1-(Ar)cyclopropyl | II | CH | O |
| 1.71 | 2-(Ar)cyclopropyl | II | CH | O |
| 1.72 | l-(2'-ClAr)cyclopropyl | II | CH | O |
| 1.73 | 2-(2'-ClAr)cyclopropyl | II | CH | O |
| 1.74 | 1-(3'-ClAr)cyclopropyl | II | CH | O |
| 1.75 | 2-(3'-ClAr)cyclopropyl | II | CH | O |
| 1.76 | 1-(4'-ClAr)cyclopropyl | II | CH | O |
| 1.77 | 2-(4'-ClAr)cyclopropyl | II | CH | O |
| 1.78 | 1-(2'-FAr)cyclopropyl | II | CH | O |
| 1.79 | 2-(2'-FAr)cyclopropyl | II | CH | O |
| 1.80 | 2-(3'-FAr)cyclopropyl | II | CH | O |
| 1.81 | 2-(4'-FAr)cyclopropyl | II | CH | O |
| 1.82 | 2-(2'-BrAr)cyclopropyl | II | CH | O |
| 1.83 | 2-(3'-BrAr)cyclopropyl | II | CH | O |
| 1.84 | 2-(4'-BrAr)cyclopropyl | II | CH | O |
| 1.85 | 2-(2'-FAr)cyclopropyl | II | CH | O |
| 1.86 | 2-(2'-CH₃Ar)cyclopropyl | II | CH | O |
| 1.87 | 2-(3'-CH₃Ar)cyclopropyl | II | CH | O |

TABLE 1-continued

| Cmpd# | R | Formula | A | V |
|---|---|---|---|---|
| 1.88 | 2-(4'-CH$_3$Ar)cyclopropyl | II | CH | O |
| 1.89 | 2-(2'-CF$_3$Ar)cyclopropyl | II | CH | O |
| 1.90 | 2-(3'-CF$_3$Ar)cyclopropyl | II | CH | O |
| 1.91 | 2-(4'-CF$_3$Ar)cyclopropyl | II | CH | O |
| 1.92 | 1-Arcyclopentyl | II | CH | O |
| 1.93 | 1-Arcyclohexyl | II | CH | O |
| 1.94 | 2-Arcyclopentyl | II | CH | O |
| 1.95 | 2-Arcyclohexyl | II | CH | O |
| 1.96 | 2(2-Arcyclopropyl)cyclopropyl | II | CH | O |
| 1.97 | 2(1-Arcyclopropyl)cyclopropyl | II | CH | O |
| 1.98 | ArCH$_2$ | II | CH | O |
| 1.99 | 2-ClArCH$_2$ | II | CH | O |
| 1.100 | 3-ClArCH$_2$ | II | CH | O |
| 1.101 | 4-ClArCH$_2$ | II | CH | O |
| 1.102 | 2-CH$_3$ArCH$_2$ | II | CH | O |
| 1.103 | 3-CH$_3$ArCH$_2$ | II | CH | O |
| 1.104 | 4-CH$_3$ArCH$_2$ | II | CH | O |
| 1.105 | 2-(ArCH$_2$)cyclopropyl | II | CH | O |
| 1.106 | 2-(2'-ClArCH$_2$)cyclopropyl | II | CH | O |
| 1.107 | 2-(4'-ClArCH$_2$)cyclopropyl | II | CH | O |
| 1.108 | 2-(2-ArCH$_2$cyclopropyl)cyclopropyl | II | CH | O |
| 1.109 | 2-(1-ArCH$_2$cyclopropyl)cyclopropyl | II | CH | O |
| 1.110 | 2-(2-pyridyl)cyclopropyl | II | CH | O |

Further typical compounds described by the present invention are described in the following tables.

Table II

Compounds 2.1 to 2.110 are Compounds of Table 1 of Formula II, III, IV where V=O and A is N Ex. 2.01, 2.10, 2.20, 2.21 −7:3 transcis, 2.34, 2.38, 2.45, 2.48 −:3 trans/cis, Table III Compounds 3.1 to 3.110 are Compounds of Table 1 of Formula II, III, IV where V=NH and A is N Ex. 3.01, 3.10, 3.13, 3.20, 3.21, 3.34, 3.38, 3.45, 3.48 −10:1 trans/cis.

Typical compounds encompassed by the present invention of Formula I include those compounds presented in Table IV of Formula V, VI and VII where X=H. and R$_1$=R$_2$=R$_3$=R$_4$=H and n=0 and m=1.

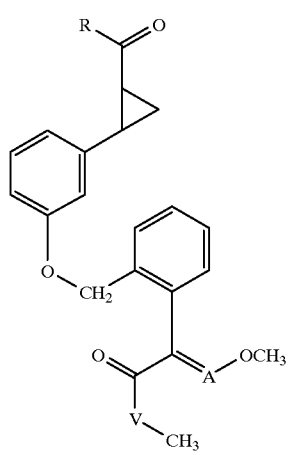

V

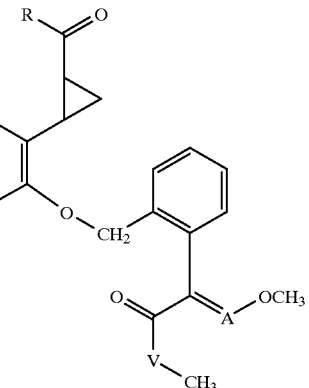

VI

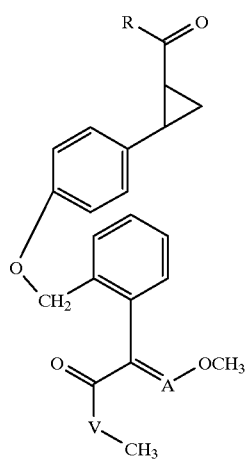

VII

TABLE IV

| Cmpd# | R | Formula | A | V |
|---|---|---|---|---|
| 4.01 | Ar | V | CH | O |
| 4.02 | Ar | VI | CH | O |
| 4.03 | Ar | VII | CH | O |
| 4.04 | 4-Cl(Ar) | V | CH | O |
| 4.05 | 4-Cl(Ar) | VI | CH | O |
| 4.06 | 4-Cl(Ar) | VII | CH | O |
| 4.07 | 2-Cl(Ar) | V | CH | O |
| 4.08 | 3-Cl(Ar) | VI | CH | O |
| 4.09 | 2-F(Ar) | V | CH | O |
| 4.10 | 4-FAr) | V | CH | O |
| 4.11 | 2-CH3(Ar) | V | CH | O |
| 4.12 | 3-CH3(Ar) | V | CH | O |
| 4.13 | 4-CH$_3$(Ar) | V | CH | O |
| 4.14 | 4-CH$_3$O(Ar) | V | CH | O |
| 4.15 | 2-CH$_3$O(Ar) | V | CH | O |
| 4.16 | 3-CH$_3$O(Ar) | V | CH | O |
| 4.17 | 2,4-Cl(Ar) | V | CH | O |
| 4.18 | CH$_3$ | V | CH | O |
| 4.19 | CH$_3$CH$_2$ | V | CH | O |
| 4.20 | CH$_3$CH$_2$CH$_2$ | V | CH | O |
| 4.21 | (CH$_3$)$_2$CH | V | CH | O |
| 4.22 | CH$_3$(CH$_2$)$_2$CH$_2$ | V | CH | O |
| 4.23 | CH$_3$(CH$_2$)$_4$CH$_2$ | V | CH | O |
| 4.24 | (CH$_3$)$_2$CHCH$_2$ | V | CH | O |
| 4.25 | CH$_3$CH$_2$(CH$_3$)CH | V | CH | O |
| 4.26 | (CH$_3$)$_3$C | V | CH | O |
| 4.27 | (CH$_3$)CHCH$_2$CH$_2$ | V | CH | O |
| 4.28 | CH$_3$CH$_2$CH(CH$_3$) | V | CH | O |
| 4.29 | CH$_3$CH$_2$(CH3)$_2$C | V | CH | O |
| 4.30 | CH$_2$=CHCH$_2$CH$_2$ | V | CH | O |

TABLE IV-continued

| Cmpd# | R | Formula | A | V |
|---|---|---|---|---|
| 4.31 | CH$_2$=C(CH$_3$)CH$_2$CH$_2$ | V | CH | O |
| 4.32 | CF$_3$CH$_2$ | V | CH | O |
| 4.33 | CH$_2$=CH | V | CH | O |
| 4.34 | cyclopropyl | V | CH | O |
| 4.35 | cyclopentyl | V | CH | O |
| 4.36 | cyclohexyl | V | CH | O |
| 4.37 | CH$_2$OCH$_3$ | V | CH | O |
| 4.38 | CH$_3$S—CH(CH$_3$) | V | CH | O |
| 4.39 | CH$_2$CH$_2$CCOAr | V | CH | O |
| 4.40 | CH$_2$OCH$_2$Ar | V | CH | O |
| 4.41 | pyridin-2-yl | V | CH | O |
| 4.42 | pyridin-3-yl | V | CH | O |
| 4.43 | pyrimidin-2-yl | V | CH | O |
| 4.44 | pyrimidin-4-yl | V | CH | O |
| 4.45 | thien-2-yl | V | CH | O |
| 4.46 | thien-3-yl | V | CH | O |
| 4.47 | 2-napthyl | V | CH | O |
| 4.48 | 2-furyl | V | CH | O |
| 4.49 | 3-furyl | V | CH | O |
| 4.50 | 2-methylcyclopropyl | V | CH | O |
| 4.51 | 2-ethylcyclopropyl | V | CH | O |
| 4.52 | 2-(n-propyl)cyclopropyl | V | CH | O |
| 4.53 | 2-(n-butyl)cyclopropyl | V | CH | O |
| 4.54 | 2-(iso-butyl)cyclopropyl | V | CH | O |
| 4.55 | 2-(sec-butyl)cyclopropyl | V | CH | O |
| 4.56 | 2-(n-pentyl)cyclopropyl | V | CH | O |
| 4.57 | 2-(iso-pentyl)cyclopropyl | V | CH | O |
| 4.58 | 2-(n-hexyl)cyclopropyl | V | CH | O |
| 4.59 | 2-methoxycyclopropyl | V | CH | O |
| 4.60 | 2-(CH$_3$O)cyclopropyl | V | CH | O |
| 4.61 | 2-(CH$_3$CH$_2$O)cyclopropyl | V | CH | O |
| 4.62 | 1-methylcyclopropyl | V | CH | O |
| 4.63 | 2-(CH$_2$=CH$_2$)cyclopropyl | V | CH | O |
| 4.64 | 1-(cyclopropyl)cyclopropyl | V | CH | O |
| 4.65 | 2-(cyclopropyl)cyclopropyl | V | CH | O |
| 4.66 | cyclopropyl-CH$_2$— | V | CH | O |
| 4.67 | cyclopropyl-CH=CH— | V | CH | O |
| 4.68 | 2-((2'-CH$_3$)cyclopropyl)cyclopropyl | V | CH | O |
| 4.69 | 2-(2'-CH$_2$=CH$_2$)cyclopropylcyclopropyl | V | CH | O |
| 4.70 | 1-Arcyclopropyl | V | CH | O |
| 4.71 | 2-Arcyclopropyl | V | CH | O |
| 4.72 | 1-(2'-ClAr)cyclopropyl | V | CH | O |
| 4.73 | 2-(2'-ClAr)cyclopropyl | V | CH | O |
| 4.74 | 1-(3'-ClAr)cyclopropyl | V | CH | O |
| 4.75 | 2-(3'-ClAr)cyclopropyl | V | CH | O |
| 4.76 | 1-(4'-ClAr)cyclopropyl | V | CH | O |
| 4.77 | 2-(4'-ClAr)cyclopropyl | V | CH | O |
| 4.78 | 1-(2'-FAr)cyclopropyl | V | CH | O |
| 4.79 | 2-(2'-FAr)cyclopropyl | V | CH | O |
| 4.80 | 2-(3'-FAr)cyclopropyl | V | CH | O |
| 4.81 | 2-(4'-FAr)cyclopropyl | V | CH | O |
| 4.82 | 2-(2'-BrAr)cyclopropyl | V | CH | O |
| 4.83 | 2-(3'-BrAr)cyclopropyl | V | CH | O |
| 4.84 | 2-(4'-BrAr)cyclopropyl | V | CH | O |
| 4.85 | 2-(2'-FAr)cyclopropyl | V | CH | O |
| 4.86 | 2-(2'-CH$_3$Ar)cyclopropyl | V | CH | O |
| 4.87 | 2-(3'-CH$_3$Ar)cyclopropyl | V | CH | O |
| 4.88 | 2-(4'-CH$_3$Ar)cyclopropyl | V | CH | O |
| 4.89 | 2-(2'-CF$_3$Ar)cyclopropyl | V | CH | O |
| 4.90 | 2-(3'-CF$_3$Ar)cyclopropyl | V | CH | O |
| 4.91 | 2-(4'-CF$_3$Ar)cyclopropyl | V | CH | O |
| 4.92 | 1-Arcyclopentyl | V | CH | O |
| 4.93 | 1-Arcyclohexyl | V | CH | O |
| 4.94 | 2-Arcyclopentyl | V | CH | O |
| 4.95 | 2-Arcyclohexyl | V | CH | O |
| 4.96 | 2(2-Arcyclopropyl)cyclopropyl | V | CH | O |
| 4.97 | 2(1-Arcyclopropyl)cyclopropyl | V | CH | O |
| 4.98 | ArCH$_2$ | V | CH | O |
| 4.99 | 2-ClArCH$_2$ | V | CH | O |
| 4.100 | 3-ClArCH$_2$ | V | CH | O |
| 4.101 | 4-ClArCH$_2$ | V | CH | O |
| 4.102 | 2-CH$_3$ArCH$_2$ | V | CH | O |
| 4.103 | 3-CH$_3$ArCH$_2$ | V | CH | O |
| 4.104 | 4-CH$_3$ArCH$_2$ | V | CH | O |
| 4.105 | 2-(ArCH$_2$)cyclopropyl | V | CH | O |
| 4.106 | 2-(2'-ClArCH$_2$)cyclopropyl | V | CH | O |
| 4.107 | 2-(4'-ClArCH$_2$)cyclopropyl | V | CH | O |
| 4.108 | 2-(2-ArCH$_2$cyclopropyl)cyclopropyl | V | CH | O |
| 4.109 | 2-(1-ArCH$_2$cyclopropyl)cyclopropyl | V | CH | O |
| 4.110 | 2-(2-pyridyl)cyclopropyl | V | CH | O |

Further typical compounds described by the present invention are described in the following tables.

Table V

Compounds 5.1 to 5.110 are Compounds of Table IV of Formula V, VI, VII where V=O and A is N Ex. 5.01, 5.04, 5.12, 5.15, 5.16, 5.17, 5.21, 5.22, 5.28, 5.30, 5.31, 5.34, Ex., 5.38, 5.62

Table VI

Compounds 6.1 to 6.110 are Compounds of Table IV of Formula V, VI, VII where V=NH and A is N Ex. 6.01, 6.04, 6.07, 6.11, 6.12, 6.15, 6.16, 6.17, 6.22, 6.24, 6.28, 6.31, 6.34, 6.38, 6.62.

Typical compounds encompassed by the present invention of Formula I include those compounds presented in Table VII of Formula VIII, IX and X where X=H. and R$_1$=R$_2$=R$_3$=R$_4$=H and n=1 and m=0.

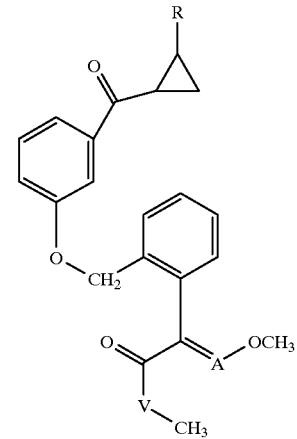

VIII

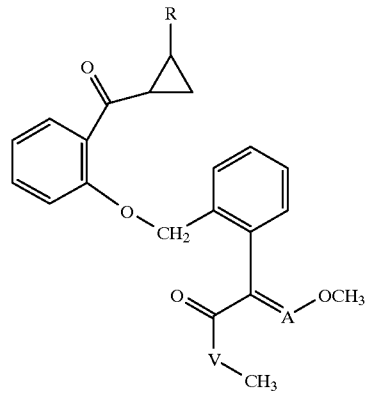

IX

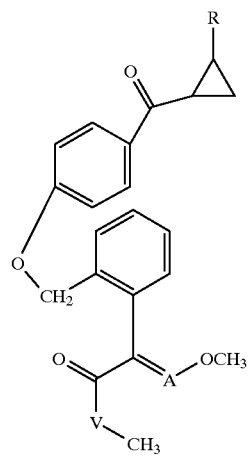

TABLE VII

| Cmpd# | R | Formula | A | V |
|---|---|---|---|---|
| 7.01 | Ar | VIII | CH | O |
| 7.02 | Ar | IX | CH | O |
| 7.03 | Ar | X | CH | O |
| 7.04 | 4-Cl(Ar) | VIII | CH | O |
| 7.05 | 4-Cl(Ar) | IX | CH | O |
| 7.06 | 4-Cl(Ar) | X | CH | O |
| 7.07 | 2-Cl(Ar) | VIII | CH | O |
| 7.08 | 3-Cl(Ar) | IX | CH | O |
| 7.09 | 2-F(Ar) | VIII | CH | O |
| 7.10 | 4-F(Ar) | VIII | CH | O |
| 7.11 | 2-CH3(Ar) | VIII | CH | O |
| 7.12 | 3-CH3(Ar) | VIII | CH | O |
| 7.13 | 4-CH$_3$(Ar) | VIII | CH | O |
| 7.14 | 4-CH$_3$O(Ar) | VIII | CH | O |
| 7.15 | 2-CH$_3$O(Ar) | VIII | CH | O |
| 7.16 | 2,5-Cl(Ar) | VIII | CH | O |
| 7.17 | 3,4-Cl(Ar) | VIII | CH | O |
| 7.18 | CH$_3$ | VIII | CH | O |
| 7.19 | CH$_3$CH$_2$ | VIII | CH | O |
| 7.20 | CH$_3$CH$_2$CH$_2$ | VIII | CH | O |
| 7.21 | (CH$_3$)$_2$CH | VIII | CH | O |
| 7.22 | CH$_3$(CH$_2$)$_2$CH$_2$ | VIII | CH | O |
| 7.23 | CH$_3$(CH$_2$)$_4$CH$_2$ | VIII | CH | O |
| 7.24 | (CH$_3$)$_2$CHCH$_2$ | VIII | CH | O |
| 7.25 | CH$_3$CH$_2$(CH$_3$)CH | VIII | CH | O |
| 7.26 | (CH$_3$)$_3$C | VIII | CH | O |
| 7.27 | (CH$_3$)CHCH$_2$CH$_2$ | VIII | CH | O |
| 7.28 | CH$_3$CH$_2$CH$_2$(CH$_3$)CH | VIII | CH | O |
| 7.29 | CH$_3$CH$_2$(CH3)$_2$C | VIII | CH | O |
| 7.30 | CF$_3$ | VIII | CH | O |
| 7.31 | CF$_3$CF$_2$ | VIII | CH | O |
| 7.32 | CF$_3$CH$_2$ | VIII | CH | O |
| 7.33 | CH$_2$=CH | VIII | CH | O |
| 7.34 | cyclopropyl | VIII | CH | O |
| 7.35 | cyclopentyl | VIII | CH | O |
| 7.36 | cyclohexyl | VIII | CH | O |
| 7.37 | CH$_2$=(cyclopropyl)C | VIII | CH | O |
| 7.38 | CH$_3$—CH=(cyclopropyl)C | VIII | CH | O |
| 7.39 | CH$_3$O—CH=(cyclopropyl)C | VIII | CH | O |
| 7.40 | C$_2$H$_5$—CH=(cyclopropyl)C | VIII | CH | O |
| 7.41 | CH$_2$=(CH(CH$_3$)$_2$)C | VIII | CH | O |
| 7.42 | CH$_3$CH=C(CH(CH$_3$)$_2$)C | VIII | CH | O |
| 7.43 | pyridin-3-yl | VIII | CH | O |
| 7.44 | pyrimidin-2-yl | VIII | CH | O |
| 7.45 | thien-2-yl | VIII | CH | O |
| 7.46 | thien-3-yl | VIII | CH | O |
| 7.47 | 2-napthyl | VIII | CH | O |
| 7.48 | 2-furyl | VIII | CH | O |
| 7.49 | 3-furyl | VIII | CH | O |
| 7.50 | 2-methylcyclopropyl | VIII | CH | O |

TABLE VII-continued

| Cmpd# | R | Formula | A | V |
|---|---|---|---|---|
| 7.51 | 2-ethylcyclopropyl | VIII | CH | O |
| 7.52 | 2-(n-propyl)cyclopropyl | VIII | CH | O |
| 7.53 | 2-(n-butyl)cyclopropyl | VIII | CH | O |
| 7.54 | 2-(iso-butyl)cyclopropyl | VIII | CH | O |
| 7.55 | 2-(sec-butyl)cyclopropyl | VIII | CH | O |
| 7.56 | 2-(n-pentyl)cyclopropyl | VIII | CH | O |
| 7.57 | 2-(iso-pentyl)cyclopropyl | VIII | CH | O |
| 7.58 | 2-(n-hexyl)cyclopropyl | VIII | CH | O |
| 7.59 | 2-methoxycyclopropyl | VIII | CH | O |
| 7.60 | 2-(CH$_3$O)cyclopropyl | VIII | CH | O |
| 7.61 | 2-(CH$_3$CH$_2$O)cyclopropyl | VIII | CH | O |
| 7.62 | 1-methylcyclopropyl | VIII | CH | O |
| 7.63 | 2-(CH$_2$=CH$_2$)cyclopropyl | VIII | CH | O |
| 7.64 | 1-(cyclopropyl)cyclopropyl | VIII | CH | O |
| 7.65 | 2-(cyclopropyl)cyclopropyl | VIII | CH | O |
| 7.66 | cyclopropyl-CH$_2$— | VIII | CH | O |
| 7.67 | cyclopropyl-CH=CH— | VIII | CH | O |
| 7.68 | 2-((2'-CH$_3$)cyclopropyl)cyclopropyl | VIII | CH | O |
| 7.69 | 2-(2'-CH$_2$=CH$_2$)cyclopropylcyclopropyl | VIII | CH | O |
| 7.70 | 1-Arcyclopropyl | VIII | CH | O |
| 7.71 | 2-Arcyclopropyl | VIII | CH | O |
| 7.72 | 1-(2'-ClAr)cyclopropyl | VIII | CH | O |
| 7.73 | 2-(2'-ClAr)cyclopropyl | VIII | CH | O |
| 7.74 | 1-(3'-ClAr)cyclopropyl | VIII | CH | O |
| 7.75 | 2-(3'-ClAr)cyclopropyl | VIII | CH | O |
| 7.76 | 1-(4'-ClAr)cyclopropyl | VIII | CH | O |
| 7.77 | 2-(4'-ClAr)cyclopropyl | VIII | CH | O |
| 7.78 | 1-(2'-FAr)cyclopropyl | VIII | CH | O |
| 7.79 | 2-(2'-FAr)cyclopropyl | VIII | CH | O |
| 7.80 | 2-(3'-FAr)cyclopropyl | VIII | CH | O |
| 7.81 | 2-(4'-FAr)cyclopropyl | VIII | CH | O |
| 7.82 | 2-(2'-BrAr)cyclopropyl | VIII | CH | O |
| 7.83 | 2-(3'-BrAr)cyclopropyl | VIII | CH | O |
| 7.84 | 2-(4'-BrAr)cyclopropyl | VIII | CH | O |
| 7.85 | 2-(2'-FAr)cyclopropyl | VIII | CH | O |
| 7.86 | 2-(2'-CH$_3$Ar)cyclopropyl | VIII | CH | O |
| 7.87 | 2-(3'-CH$_3$Ar)cyclopropyl | VIII | CH | O |
| 7.88 | 2-(4'-CH$_3$Ar)cyclopropyl | VIII | CH | O |
| 7.89 | 2-(2'-CF$_3$Ar)cyclopropyl | VIII | CH | O |
| 7.90 | 2-(3'-CF$_3$Ar)cyclopropyl | VIII | CH | O |
| 7.91 | 2-(4'-CF$_3$Ar)cyclopropyl | VIII | CH | O |
| 7.92 | 1-Arcyclopentyl | VIII | CH | O |
| 7.93 | 1-Arcyclohexyl | VIII | CH | O |
| 7.94 | 2-Arcyclopentyl | VIII | CH | O |
| 7.95 | 2-Arcyclohexyl | VIII | CH | O |
| 7.96 | 2(2-Arcyclopropyl)cyclopropyl | VIII | CH | O |
| 7.97 | 2(1-Arcyclopropyl)cyclopropyl | VIII | CH | O |
| 7.98 | ArCH$_2$ | VIII | CH | O |
| 7.99 | 2-ClArCH$_2$ | VIII | CH | O |
| 7.100 | 3-ClArCH$_2$ | VIII | CH | O |
| 7.101 | 4-ClArCH$_2$ | VIII | CH | O |
| 7.102 | 2-CH$_3$ArCH$_2$ | VIII | CH | O |
| 7.103 | 3-CH$_3$ArCH$_2$ | VIII | CH | O |
| 7.104 | 4-CH$_3$ArCH$_2$ | VIII | CH | O |
| 7.105 | 2-(ArCH$_2$)cyclopropyl | VIII | CH | O |
| 7.106 | 2-(2'-ClArCH$_2$)cyclopropyl | VIII | CH | O |
| 7.107 | 2-(4'-ClArCH$_2$)cyclopropyl | VIII | CH | O |
| 7.108 | 2-(2-ArCH$_2$cyclopropyl)cyclopropyl | VIII | CH | O |
| 7.109 | 2-(1-ArCH$_2$cyclopropyl)cyclopropyl | VIII | CH | O |
| 7.110 | 2-(2-pyridyl)cyclopropyl | VIII | CH | O |

Further typical compounds described by the present invention are described in the following tables.

Table VIII

Compounds 8.1 to 8.110 are Compounds of Table VII of Formula VIII, IX, X where V=O and A is N.

Table IX

Compounds 9.1 to 9.110 are Compounds of Table VII of Formula VIII, IX, X where V=NH and A is N.

Typical compounds encompassed by the present invention of Formula I include those compounds presented in Table X of Formula XI, XII and XIII where X=H and one of $R_1$ or $R_2$ or $R_3$ or $R_4$ is not H and n=0 or 1, m=0 or 1 and n+m=0 or 1.

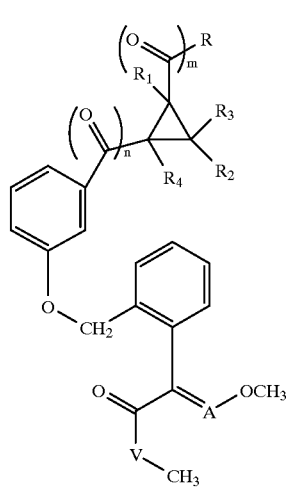
XI

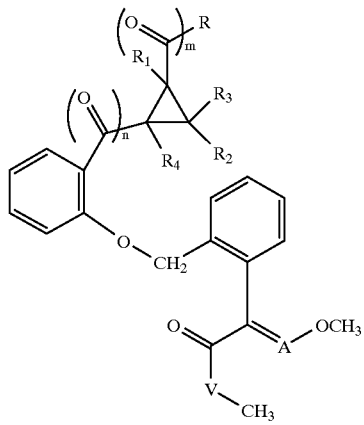
XII

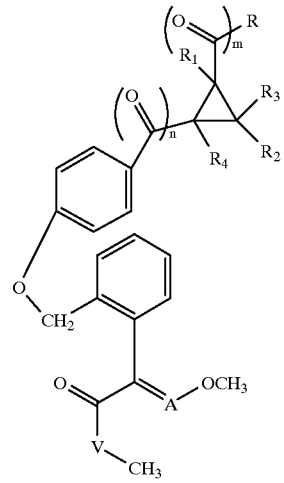
XIII

TABLE X

| Cmpd # | R | Formula | n | m | $R_1$ | $R_2$ | $R_3$ | $R_4$ | A | V |
|---|---|---|---|---|---|---|---|---|---|---|
| 10.01 | Ar | XI | 0 | 0 | CN | H | H | H | CH | O |
| 10.02 | Ar | XII | 0 | 0 | CN | H | H | H | CH | O |
| 10.03 | Ar | XIII | 0 | 0 | CN | H | H | H | CH | O |
| 10.04 | 4-Cl(Ar) | XI | 0 | 0 | CN | H | H | H | CH | O |
| 10.05 | 4-Cl(Ar) | XII | 0 | 0 | CN | H | H | H | CH | O |
| 10.06 | 4-Cl(Ar) | XIII | 0 | 0 | CN | H | H | H | CH | O |
| 10.07 | 2-F(Ar) | XI | 0 | 0 | CN | H | H | H | CH | O |
| 10.08 | 4-$CH_3$(Ar) | XI | 0 | 0 | CN | H | H | H | CH | O |
| 10.09 | 4-$CH_3$O(Ar) | XI | 0 | 0 | CN | H | H | H | CH | O |
| 10.10 | 2,4-Cl(Ar) | XI | 0 | 0 | CN | H | H | H | CH | O |
| 10.11 | $CH_3$ | XI | 0 | 0 | CN | H | H | H | CH | O |
| 10.12 | $CH_3CH_2$ | XI | 0 | 0 | CN | H | H | H | CH | O |
| 10.13 | cyclopropyl | XI | 0 | 0 | CN | H | H | H | CH | O |
| 10.14 | pyridin-2-yl | XI | 0 | 0 | CN | H | H | H | CH | O |
| 10.15 | Ar(cyclopropyl) | XI | 0 | 0 | CN | H | H | H | CH | O |
| 10.16 | Ar | XI | 0 | 0 | $CO_2Et$ | H | H | H | CH | O |
| 10.17 | Ar | XII | 0 | 0 | $CO_2Et$ | H | H | H | CH | O |
| 10.18 | Ar | XIII | 0 | 0 | $CO_2Et$ | H | H | H | CH | O |
| 10.19 | 4-Cl(Ar) | XI | 0 | 0 | $CO_2Et$ | H | H | H | CH | O |
| 10.20 | 2-F(Ar) | XI | 0 | 0 | $CO_2Et$ | H | H | H | CH | O |
| 10.21 | 4-$CH_3$(Ar) | XI | 0 | 0 | $CO_2Et$ | H | H | H | CH | O |
| 10.22 | 4-$CH_3$O(Ar) | XI | 0 | 0 | $CO_2Et$ | H | H | H | CH | O |
| 10.23 | 2,4-Cl(Ar) | XI | 0 | 0 | $CO_2Et$ | H | H | H | CH | O |
| 10.24 | $CH_3$ | XI | 0 | 0 | $CO_2Et$ | H | H | H | CH | O |
| 10.25 | $CH_3CH_2$ | XI | 0 | 0 | $CO_2Et$ | H | H | H | CH | O |
| 10.26 | cyclopropyl | XI | 0 | 0 | $CO_2Et$ | H | H | H | CH | O |

TABLE X-continued

| Cmpd # | R | Formula | n | m | R₁ | R₂ | R₃ | R₄ | A | V |
|---|---|---|---|---|---|---|---|---|---|---|
| 10.27 | pyridin-2-yl | XI | 0 | 0 | CO₂Et | H | H | H | CH | O |
| 10.28 | Ar(cyclopropyl) | XI | 0 | 0 | CO₂Et | H | H | H | CH | O |
| 10.29 | Ar | XI | 0 | 0 | H | CN | H | H | CH | O |
| 10.30 | Ar | XII | 0 | 0 | H | CN | H | H | CH | O |
| 10.31 | Ar | XIII | 0 | 0 | H | CN | H | H | CH | O |
| 10.32 | 4-Cl(Ar) | XI | 0 | 0 | H | CN | H | H | CH | O |
| 10.33 | 4-Cl(Ar) | XII | 0 | 0 | H | CN | H | H | CH | O |
| 10.34 | 4-Cl(Ar) | XIII | 0 | 0 | H | CN | H | H | CH | O |
| 10.35 | 2-F(Ar) | XI | 0 | 0 | H | CN | H | H | CH | O |
| 10.36 | 4-CH₃(Ar) | XI | 0 | 0 | H | CN | H | H | CH | O |
| 10.37 | 4-CH₃O(Ar) | XI | 0 | 0 | H | CN | H | H | CH | O |
| 10.38 | 2,4-Cl(Ar) | XI | 0 | 0 | H | CN | H | H | CH | O |
| 10.39 | CH₃ | XI | 0 | 0 | H | CN | H | H | CH | O |
| 10.40 | CH₃CH₂ | XI | 0 | 0 | H | CN | H | H | CH | O |
| 10.41 | cyclopropyl | XI | 0 | 0 | H | CN | H | H | CH | O |
| 10.42 | pyridin-2-yl | XI | 0 | 0 | H | CN | H | H | CH | O |
| 10.43 | Ar(cyclopropyl) | XI | 0 | 0 | H | CN | H | H | CH | O |
| 10.44 | Ar | XI | 0 | 0 | H | CO₂Et | H | H | CH | O |
| 10.45 | Ar | XII | 0 | 0 | H | CO₂Et | H | H | CH | O |
| 10.46 | Ar | XIII | 0 | 0 | H | CO₂Et | H | H | CH | O |
| 10.47 | 4-Cl(Ar) | XI | 0 | 0 | H | CO₂Et | H | H | CH | O |
| 10.48 | 4-Cl(Ar) | XII | 0 | 0 | H | CO₂Et | H | H | CH | O |
| 10.49 | 4-Cl(Ar) | XIII | 0 | 0 | H | CO₂Et | H | H | CH | O |
| 10.50 | 2-F(Ar) | XI | 0 | 0 | H | CO₂Et | H | H | CH | O |
| 10.51 | 4-CH₃(Ar) | XI | 0 | 0 | H | CO₂Et | H | H | CH | O |
| 10.52 | 4-CH₃O(Ar) | XI | 0 | 0 | H | CO₂Et | H | H | CH | O |
| 10.53 | 2,4-Cl(Ar) | XI | 0 | 0 | H | CO₂Et | H | H | CH | O |
| 10.54 | CH₃ | XI | 0 | 0 | H | CO₂Et | H | H | CH | O |
| 10.55 | CH₃CH₂ | XI | 0 | 0 | H | CO₂Et | H | H | CH | O |
| 10.56 | cyclopropyl | XI | 0 | 0 | H | CO₂Et | H | H | CH | O |
| 10.57 | pyridin-2-yl | XI | 0 | 0 | H | CO₂Et | H | H | CH | O |
| 10.58 | Ar(cyclopropyl) | XI | 0 | 0 | H | CO₂Et | H | H | CH | O |
| 10.59 | Ar | XI | 0 | 0 | H | H | H | CN | CH | O |
| 10.60 | Ar | XII | 0 | 0 | H | H | H | CN | CH | O |
| 10.61 | Ar | XIII | 0 | 0 | H | H | H | CN | CH | O |
| 10.62 | 4-Cl(Ar) | XI | 0 | 0 | H | H | H | CN | CH | O |
| 10.63 | 4-Cl(Ar) | XI | 0 | 0 | H | H | H | CN | CH | O |
| 10.64 | 4-Cl(Ar) | XI | 0 | 0 | H | H | H | CN | CH | O |
| 10.65 | 2-F(Ar) | XI | 0 | 0 | H | H | H | CN | CH | O |
| 10.66 | 4-CH₃(Ar) | XI | 0 | 0 | H | H | H | CN | CH | O |
| 10.67 | 4-CH₃O(Ar) | XI | 0 | 0 | H | H | H | CN | CH | O |
| 10.68 | 2,4-Cl(Ar) | XI | 0 | 0 | H | H | H | CN | CH | O |
| 10.69 | CH₃ | XII | 0 | 0 | H | H | H | CN | CH | O |
| 10.70 | CH₃CH₂ | XIII | 0 | 0 | H | H | H | CN | CH | O |
| 10.71 | cyclopropyl | XI | 0 | 0 | H | H | H | CN | CH | O |
| 10.72 | pyridin-2-yl | XII | 0 | 0 | H | H | H | CN | CH | O |
| 10.73 | Ar(cyclopropyl) | XIII | 0 | 0 | H | H | H | CN | CH | O |
| 10.74 | Ar | XI | 0 | 0 | H | H | H | CO₂Et | CH | O |
| 10.75 | Ar | XII | 0 | 0 | H | H | H | CO₂Et | CH | O |
| 10.76 | Ar | XIII | 0 | 0 | H | H | H | CO₂Et | CH | O |
| 10.77 | 4-Cl(Ar) | XI | 0 | 0 | H | H | H | CO₂Et | CH | O |
| 10.78 | 2-F(Ar) | XI | 0 | 0 | H | H | H | CO₂Et | CH | O |
| 10.79 | 4-CH₃(Ar) | XI | 0 | 0 | H | H | H | CO₂Et | CH | O |
| 10.80 | 4-CH₃O(Ar) | XI | 0 | 0 | H | H | H | CO₂Et | CH | O |
| 10.81 | 2,4-Cl(Ar) | XI | 0 | 0 | H | H | H | CO₂Et | CH | O |
| 10.82 | CH₃ | XI | 0 | 0 | H | H | H | CO₂Et | CH | O |
| 10.83 | CH₃CH₂ | XI | 0 | 0 | H | H | H | CO₂Et | CH | O |
| 10.84 | cyclopropyl | XI | 0 | 0 | H | H | H | CO₂Et | CH | O |
| 10.85 | pyridin-2-yl | XI | 0 | 0 | H | H | H | CO₂Et | CH | O |
| 10.86 | Ar(cyclopropyl) | XI | 0 | 0 | H | H | H | CO₂Et | CH | O |
| 10.87 | Ar | XI | 0 | 1 | CN | H | H | H | CH | O |
| 10.88 | Ar | XII | 0 | 1 | CN | H | H | H | CH | O |
| 10.89 | Ar | XIII | 0 | 1 | CN | H | H | H | CH | O |
| 10.90 | 4-Cl(Ar) | XI | 0 | 1 | CN | H | H | H | CH | O |
| 10.91 | 2-F(Ar) | XI | 0 | 1 | CN | H | H | H | CH | O |
| 10.92 | 4-CH₃(Ar) | XI | 0 | 1 | CN | H | H | H | CH | O |
| 10.93 | 4-CH₃O(Ar) | XI | 0 | 1 | CN | H | H | H | CH | O |
| 10.94 | 2,4-Cl(Ar) | XI | 0 | 1 | CN | H | H | H | CH | O |
| 10.95 | CH₃ | XI | 0 | 1 | CN | H | H | H | CH | O |
| 10.96 | CH₃CH₂ | XI | 0 | 1 | CN | H | H | H | CH | O |
| 10.97 | cyclopropyl | XI | 0 | 1 | CN | H | H | H | CH | O |
| 10.98 | (CH₃)₃C | XI | 0 | 1 | CN | H | H | H | CH | O |
| 10.99 | pyridin-2-yl | XI | 0 | 1 | CN | H | H | H | CH | O |
| 10.100 | Ar(cyclopropyl) | XI | 0 | 1 | CN | H | H | H | CH | O |
| 10.101 | Ar | XI | 0 | 1 | CO₂Et | H | H | H | CH | O |
| 10.102 | Ar | XII | 0 | 1 | CO₂Et | H | H | H | CH | O |
| 10.103 | Ar | XIII | 0 | 1 | CO₂Et | H | H | H | CH | O |

TABLE X-continued

| Cmpd # | R | Formula | n | m | R$_1$ | R$_2$ | R$_3$ | R$_4$ | A | V |
|---|---|---|---|---|---|---|---|---|---|---|
| 10.104 | 4-Cl(Ar) | XI | 0 | 1 | CO$_2$Et | H | H | H | CH | O |
| 10.105 | 2-F(Ar) | XI | 0 | 1 | CO$_2$Et | H | H | H | CH | O |
| 10.106 | 4-CH$_3$(Ar) | XI | 0 | 1 | CO$_2$Et | H | H | H | CH | O |
| 10.107 | 4-CH$_3$O(Ar) | XI | 0 | 1 | CO$_2$Et | H | H | H | CH | O |
| 10.108 | 2,4-Cl(Ar) | XI | 0 | 1 | CO$_2$Et | H | H | H | CH | O |
| 10.109 | CH$_3$ | XI | 0 | 1 | CO$_2$Et | H | H | H | CH | O |
| 10.110 | CH$_3$CH$_2$ | XI | 0 | 1 | CO$_2$Et | H | H | H | CH | O |
| 10.111 | cyclopropyl | XI | 0 | 1 | CO$_2$Et | H | H | H | CH | O |
| 10.112 | pyridin-2-yl | XI | 0 | 1 | CO$_2$Et | H | H | H | CH | O |
| 10.113 | Ar(cyclopropyl) | XI | 0 | 1 | CO$_2$Et | H | H | H | CH | O |
| 10.114 | Ar | XI | 0 | 1 | H | CN | H | H | CH | O |
| 10.115 | Ar | XII | 0 | 1 | H | CN | H | H | CH | O |
| 10.116 | Ar | XIII | 0 | 1 | H | CN | H | H | CH | O |
| 10.117 | 4-Cl(Ar) | XI | 0 | 1 | H | CN | H | H | CH | O |
| 10.118 | 2-F(Ar) | XI | 0 | 1 | H | CN | H | H | CH | O |
| 10.119 | 4-CH$_3$(Ar) | XI | 0 | 1 | H | CN | H | H | CH | O |
| 10.120 | 4-CH$_3$O(Ar) | XI | 0 | 1 | H | CN | H | H | CH | O |
| 10.121 | 2,4-Cl(Ar) | XI | 0 | 1 | H | CN | H | H | CH | O |
| 10.122 | CH$_3$ | XI | 0 | 1 | H | CN | H | H | CH | O |
| 10.123 | CH$_3$CH$_2$ | XI | 0 | 1 | H | CN | H | H | CH | O |
| 10.124 | cyclopropyl | XI | 0 | 1 | H | CN | H | H | CH | O |
| 10.125 | pyridin-2-yl | XI | 0 | 1 | H | CN | H | H | CH | O |
| 10.126 | Ar(cyclopropyl) | XI | 0 | 1 | H | CN | H | H | CH | O |
| 10.127 | Ar | XI | 0 | 1 | H | CO$_2$Et | H | H | CH | O |
| 10.128 | Ar | XII | 0 | 1 | H | CO$_2$Et | H | H | CH | O |
| 10.129 | Ar | XIII | 0 | 1 | H | CO$_2$Et | H | H | CH | O |
| 10.130 | 4-Cl(Ar) | XI | 0 | 1 | H | CO$_2$Et | H | H | CH | O |
| 10.131 | 2-F(Ar) | XI | 0 | 1 | H | CO$_2$Et | H | H | CH | O |
| 10.132 | 4-CH$_3$(Ar) | XI | 0 | 1 | H | CO$_2$Et | H | H | CH | O |
| 10.133 | 4-CH$_3$O(Ar) | XI | 0 | 1 | H | CO$_2$Et | H | H | CH | O |
| 10.134 | 2,4-Cl(Ar) | XI | 0 | 1 | H | CO$_2$Et | H | H | CH | O |
| 10.135 | CH$_3$ | XI | 0 | 1 | H | CO$_2$Et | H | H | CH | O |
| 10.136 | CH$_3$CH$_2$ | XI | 0 | 1 | H | CO$_2$Et | H | H | CH | O |
| 10.137 | cyclopropyl | XI | 0 | 1 | H | CO$_2$Et | H | H | CH | O |
| 10.138 | pyridin-2-yl | XI | 0 | 1 | H | CO$_2$Et | H | H | CH | O |
| 10.139 | Ar(cyclopropyl) | XI | 0 | 1 | H | CO$_2$Et | H | H | CH | O |
| 10.140 | Ar | XI | 0 | 1 | H | H | H | CN | CH | O |
| 10.141 | Ar | XII | 0 | 1 | H | H | H | CN | CH | O |
| 10.142 | Ar | XIII | 0 | 1 | H | H | H | CN | CH | O |
| 10.143 | 4-Cl(Ar) | XI | 0 | 1 | H | H | H | CN | CH | O |
| 10.144 | 2-F(Ar) | XI | 0 | 1 | H | H | H | CN | CH | O |
| 10.145 | 4-CH$_3$(Ar) | XI | 0 | 1 | H | H | H | CN | CH | O |
| 10.146 | 4-CH$_3$O(Ar) | XI | 0 | 1 | H | H | H | CN | CH | O |
| 10.147 | 2,4-Cl(Ar) | XI | 0 | 1 | H | H | H | CN | CH | O |
| 10.148 | CH$_3$ | XI | 0 | 1 | H | H | H | CN | CH | O |
| 10.149 | CH$_3$CH$_2$ | XI | 0 | 1 | H | H | H | CN | CH | O |
| 10.150 | cyclopropyl | XI | 0 | 1 | H | H | H | CN | CH | O |
| 10.151 | pyridin-2-yl | XI | 0 | 1 | H | H | H | CN | CH | O |
| 10.152 | Ar(cyclopropyl) | XI | 0 | 1 | H | H | H | CN | CH | O |
| 10.153 | Ar | XI | 0 | 1 | H | H | H | CO$_2$Et | CH | O |
| 10.154 | Ar | XII | 0 | 1 | H | H | H | CO$_2$Et | CH | O |
| 10.155 | Ar | XIII | 0 | 1 | H | H | H | CO$_2$Et | CH | O |
| 10.156 | 4-Cl(Ar) | XI | 0 | 1 | H | H | H | CO$_2$Et | CH | O |
| 10.157 | 2-F(Ar) | XI | 0 | 1 | H | H | H | CO$_2$Et | CH | O |
| 10.158 | 4-CH$_3$(Ar) | XI | 0 | 1 | H | H | H | CO$_2$Et | CH | O |
| 10.159 | 4-CH$_3$O(Ar) | XI | 0 | 1 | H | H | H | CO$_2$Et | CH | O |
| 10.160 | 2,4-Cl(Ar) | XI | 0 | 1 | H | H | H | CO$_2$Et | CH | O |
| 10.161 | CH$_3$ | XI | 0 | 1 | H | H | H | CO$_2$Et | CH | O |
| 10.162 | CH$_3$CH$_2$ | XI | 0 | 1 | H | H | H | CO$_2$Et | CH | O |
| 10.163 | cyclopropyl | XI | 0 | 1 | H | H | H | CO$_2$Et | CH | O |
| 10.164 | pyridin-2-yl | XI | 0 | 1 | H | H | H | CO$_2$Et | CH | O |
| 10.165 | Ar(cyclopropyl) | XI | 0 | 1 | H | H | H | CO$_2$Et | CH | O |
| 10.166 | Ar | XI | 0 | 1 | H | —CH$_2$CH$_2$— | | H | CH | O |
| 10.167 | Ar | XII | 0 | 1 | H | —CH$_2$CH$_2$— | | H | CH | O |
| 10.168 | Ar | XIII | 0 | 1 | H | —CH$_2$CH$_2$— | | H | CH | O |
| 10.169 | 4-Cl(Ar) | XI | 0 | 1 | H | —CH$_2$CH$_2$— | | H | CH | O |
| 10.170 | 2-F(Ar) | XI | 0 | 1 | H | —CH$_2$CH$_2$— | | H | CH | O |
| 10.171 | 4-CH$_3$(Ar) | XI | 0 | 1 | H | —CH$_2$CH$_2$— | | H | CH | O |
| 10.172 | 4-CH$_3$O(Ar) | XI | 0 | 1 | H | —CH$_2$CH$_2$— | | H | CH | O |
| 10.173 | 2,4-Cl(Ar) | XI | 0 | 1 | H | —CH$_2$CH$_2$— | | H | CH | O |
| 10.174 | CH$_3$ | XI | 0 | 1 | H | —CH$_2$CH$_2$— | | H | CH | O |
| 10.175 | CH$_3$CH$_2$ | XI | 0 | 1 | H | —CH$_2$CH$_2$— | | H | CH | O |
| 10.176 | cyclopropyl | XI | 0 | 1 | H | —CH$_2$CH$_2$— | | H | CH | O |
| 10.177 | (CH$_3$)$_3$C | XI | 0 | 1 | H | —CH$_2$CH$_2$— | | H | CH | O |
| 10.178 | pyridin-2-yl | XI | 0 | 1 | H | —CH$_2$CH$_2$— | | H | CH | O |
| 10.179 | Ar(cyclopropyl) | XI | 0 | 1 | H | —CH$_2$CH$_2$— | | H | CH | O |
| 10.180 | Ar | XI | 1 | 0 | CN | H | H | H | CH | O |

TABLE X-continued

| Cmpd # | R | Formula | n | m | R₁ | R₂ | R₃ | R₄ | A | V |
|---|---|---|---|---|---|---|---|---|---|---|
| 10.181 | Ar | XII | 1 | 0 | CN | H | H | H | CH | O |
| 10.182 | Ar | XIII | 1 | 0 | CN | H | H | H | CH | O |
| 10.183 | 4-Cl(Ar) | XI | 1 | 0 | CN | H | H | H | CH | O |
| 10.184 | 2-F(Ar) | XI | 1 | 0 | CN | H | H | H | CH | O |
| 10.185 | 4-CH₃(Ar) | XI | 1 | 0 | CN | H | H | H | CH | O |
| 10.186 | 4-CH₃O(Ar) | XI | 1 | 0 | CN | H | H | H | CH | O |
| 10.187 | 2,4-Cl(Ar) | XI | 1 | 0 | CN | H | H | H | CH | O |
| 10.188 | CH₃ | XI | 1 | 0 | CN | H | H | H | CH | O |
| 10.189 | CH₃CH₂ | XI | 1 | 0 | CN | H | H | H | CH | O |
| 10.190 | cyclopropyl | XI | 1 | 0 | CN | H | H | H | CH | O |
| 10.191 | (CH₃)₃C | XI | 1 | 0 | CN | H | H | H | CH | O |
| 10.192 | pyridin-2-yl | XI | 1 | 0 | CN | H | H | H | CH | O |
| 10.193 | Ar(cyclopropyl) | XI | 1 | 0 | CN | H | H | H | CH | O |
| 10.194 | Ar | XI | 1 | 0 | CO₂Et | H | H | H | CH | O |
| 10.195 | Ar | XII | 1 | 0 | CO₂Et | H | H | H | CH | O |
| 10.196 | Ar | XIII | 1 | 0 | CO₂Et | H | H | H | CH | O |
| 10.197 | 4-Cl(Ar) | XI | 1 | 0 | CO₂Et | H | H | H | CH | O |
| 10.198 | 2-F(Ar) | XI | 1 | 0 | CO₂Et | H | H | H | CH | O |
| 10.199 | 4-CH₃(Ar) | XI | 1 | 0 | CO₂Et | H | H | H | CH | O |
| 10.200 | 4-CH₃O(Ar) | XI | 1 | 0 | CO₂Et | H | H | H | CH | O |
| 10.201 | 2,4-Cl(Ar) | XI | 1 | 0 | CO₂Et | H | H | H | CH | O |
| 10.202 | CH₃ | XI | 1 | 0 | CO₂Et | H | H | H | CH | O |
| 10.203 | CH₃CH₂ | XI | 1 | 0 | CO₂Et | H | H | H | CH | O |
| 10.204 | cyclopropyl | XI | 1 | 0 | CO₂Et | H | H | H | CH | O |
| 10.205 | (CH₃)₃C | XI | 1 | 0 | CO₂Et | H | H | H | CH | O |
| 10.206 | pyridin-2-yl | XI | 1 | 0 | CO₂Et | H | H | H | CH | O |
| 10.207 | Ar(cyclopropyl) | XI | 1 | 0 | CO₂Et | H | H | H | CH | O |

Further typical compounds described by the present invention are described in the following tables.

Table XI

Compounds 11.1 to 11.207 are Compounds of Table X of Formula XI, XII, XIII where V=O and A is N. Examples are 11.01, 11.59, 11.137.

Table XII

Compounds 12.1 to 12.207 are Compounds of Table X of Formula XI, XII, XIII where V=NH and A is N. Examples are 12.01, 12.59.

As used in Tables 1 to 12 Ar is understood to be phenyl. The compounds of Formula I can be prepared by a variety of synthetic routes. A general overview of synthesis methods for cyclopropanes is described in March, *Advanced Organic Chemistry*, 4th Ed, pp. 866–873 and references therein.

When n and m are both zero and $R_1$ and $R_4$ are hydrogen and $R_2$ or $R_3$ are both hydrogen or independently hydrogen the compounds of formula (I) are prepared in a four step sequence shown in Scheme A. The substituted cyclopropyl phenols (XVI) are prepared from the pyrazolines (XV) which are prepared from α,β unsaturated compounds (XIV). These enones can be prepared by conventional condensation techniques. For example *Organic Reactions*, Volume 16 describes the general aldol condensation and specifically the condensation of benzaldehdydes with ketones. A hydroxybenzaldehdyde is condensed with a ketone, RCOCH₂R₂, which when R₂=H is a methyl ketone, provides the unsaturated intermediate (XIV'). Substituted hydroxybenzaldehyde such as ortho, meta or para-hydroxybenzaldehyde provides three corresponding regioisomeric intermediates XIV and XIV'. A variety of reaction conditions can be employed to prepare the enones XIV and XIV' which are described in *Organic Reactions* Vol 16 pp. 69–85. For example, a ketone is dissolved in a hydroxylic solvent, such as ethanol, to which is added dropwise a solution of the hydroxybenzaldehyde in an aqueous basic solution. The bases used can be alkali metal hydroxides, such as potassium or sodium hydroxide and the dropwise addition is conducted from 0° C. to 35° C., preferably at ambient temperature.

The intermediate enones XIV and XIV' are reacted with hydrazine to provide the intermediate XV and XV' pyrazoline. Typical preparation of pyrazolines from unsaturated enones by treatment with hydrazine are described in *Synthetic Commun*, 25(12), 1877–1883 (1995); *JACS* 73, 3840 (1951); *Indian J. Chem Soc Sect B* 98–104 (1992) and J. Indian Chem Soc 643–644 (1993). For example, in JACS 73, 3840 (1951) styryl cyclopropyl ketone is reacted with aqueous hydrazine in 95% ethanol and stirred on a steam bath for 1 hr. which after distillation gave the pyrazoline in 86% yield. Similarly in *Synthetic Commun*, 25(12), 1877–1883 (1995) chalcones are treated with hydrazine monohydrate and stirred at reflux in ethanol and gave the pyrazolines in >90% yield. The intermediate pyrazoline XV' is heated with caustic (NaOH) at 250° C. as described in *Synthetic Commun*, 25(12), and *JACS* 73, 3840 (1951) to provide the cyclopropyl phenols XVI'.

Scheme A

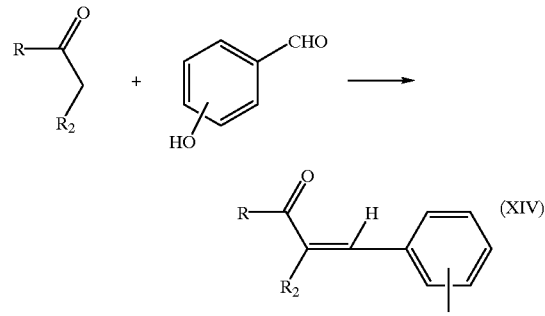

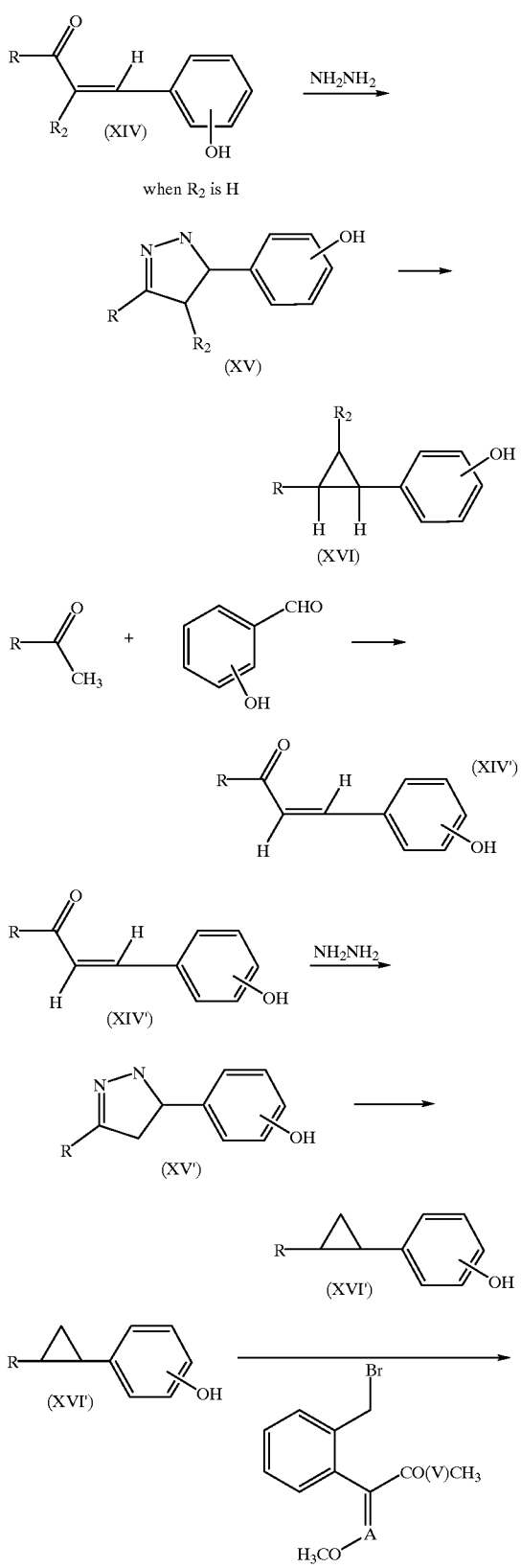

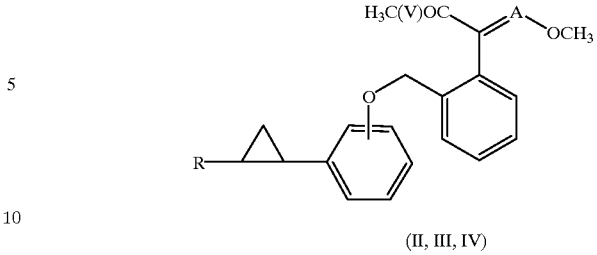

(II, III, IV)

Compounds of formula I where A is CH and V is O are prepared by alkylation with methyl E-a-(2-bromomethylphenyl)-β-methoxyacrylate in the presence of a base such as a metal hydride, preferably NaH, in an aprotic solvent such as N,N-dimethyl-formamide. Methyl E-a-(2-bromomethylphenyl)-β-methoxyacrylate, as a single E isomer, can be prepared in two steps from 2-methylphenylacetate as described previously in U.S. Pat. No. 4,914,128, columns 3–4. Compounds of formula I where A is N and V is oxygen are prepared by the reaction with methyl E-2-(bromomethyl)phenylglyoxylate O-methyloxime in the presence of a base such as a metal hydride, preferably NaH, in an aprotic solvent such as N,N dimethylformamide. Methyl 2-(bromomethyl) phenylglyoxylate O-methyloxime can be prepared as described in U.S. Pat. Nos. 4,999,042, columns 17–18 and 5,157,144, columns 17–18. Methyl 2-(bromomethyl) phenylglyoxylate O-methyloxime is prepared from methyl 2-methylphenyl-acetate by treatment with an alkyl nitrite under basic conditions to provide after methylation, methyl 2-methylphenylglyoxalate O-methyl oxime which can also be prepared from methyl 2-methylphenylglyoxalate by treatment with 2-hydroxylamine hydrochloride and methylation or by treatment with methoxylamine hydrochloride. An alternative synthetic route to examples when A is N and V is oxygen, is provided by the alkylation of cyclopropylphenols XVI' with methyl 2-(bromomethyl)phenylglyoxylate followed by reaction with methoxylamine HCl or hydroxylamine HCl followed by methylation.

The amminolysis of oximinoacetates to oximinoacetamides has been described in U.S. Pat. Nos. 5,185,342, cols. 22, 48 and 57, 5,221,691, cols. 26–27, and 5,407,902, col. 8. For example, compounds of Table 2 of formula II,II and IV where A is N and V is O are treated with 40% aqueous methylamine in methanol to provide compounds of Table 3 of formula II, III or IV where V is NH. Alternatively intermediate XVI' is reacted with N-methyl E-2-methoxyimino-2-[2-(bromomethyl)phenyl]acetamide in the presence of a base such as a metal hydride, preferably NaH, in an aprotic solvent such as dimethyl formide (DMF) to provide compounds of Table 3 of formula II, III and IV. N-methyl E-2-methoxyimino-2-[2-(bromomethyl)phenyl] acetamide is described in U.S. Pat. No. 5,387,714, col. 13.

Compounds of Tables 1,2 and 3 of formula II, III and IV are prepared by the alkylation of intermediate cyclopropyl phenols XVI' with the appropriately substituted benzyl bromides as shown in Scheme A. Alkylation of cyclopropyl phenol intermediate XVI' derived from meta-hydroxybenzaldehyde provides compounds of Tables 1–3 of Formula II.

Alkylation of intermediate XVI' derived from ortho-hydroxybenzaldehyde provides compounds of Tables 1–3 of Formula III and alkylation of intermediate XVI' derived from para-hydroxybenzaldehdyde provides compounds of Tables 1–3 of Formula IV.

Scheme B also describes the preparation of compounds of the formula (I) where. $R_1$ and $R_4$ are hydrogen and $R_2$ or $R_3$ are both hydrogen or independently hydrogen. The α,β unsaturated compounds (XVII) can be prepared by conventional condensation techniques. For example *Organic Reactions*, Volume 16 describes the general aldol condensation and specifically the condensation of aldehdydes with ketones. An aldehyde, for example a substituted benzaldehyde is condensed with an hydroxyphenylketone, (OH)ArCOCH2$R_2$, which, when $R_2$=H is a methyl ketone, provides the unsaturated intermediate XVII'.

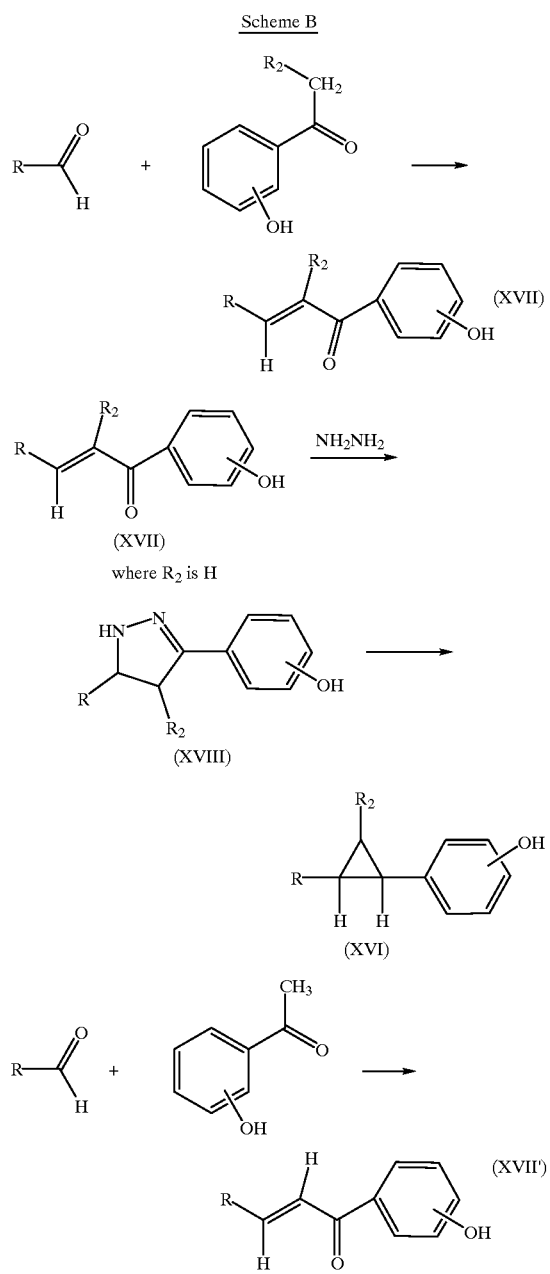

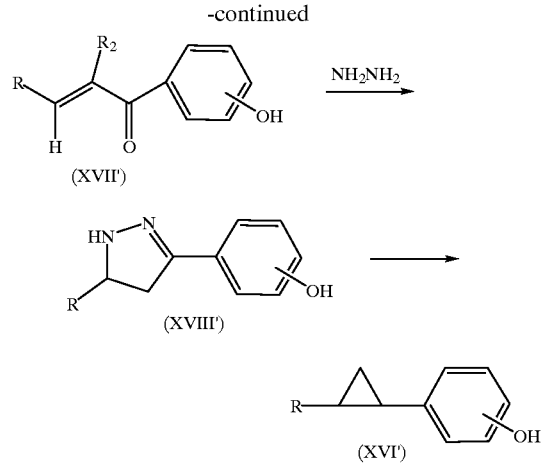

Substituted hydroxyphenylketones such as ortho, meta or para-hydroxyacetophenone provides three regioisomeric intermediates XVII ($R_2$ is not H) and XVII' where $R_2$=H. The intermediate enones XVII and XVII' are reacted with hydrazine in the same manner as intermediate XIV and XIV' (Scheme A) resulting in the cyclopropyl phenols XVI and XVI'; as described in Scheme B. The cyclopropylphenols XVI' are used to prepare compounds of Tables 1,2 and 3 of formula II, III and IV as described in Scheme A.

When n is zero and m=1 the compounds of formula (I) are prepared in three step sequence shown in Scheme C. The unsaturated intermediate XIV (scheme A) prepared by conventional condensation techniques is reacted with a sulfur ylid, prepared from a dimethylsulfoxonium salt in the presence of a base, resulting in the substituted acyl cyclopropyl phenols (MX). The chemistry of sulfur ylids is described in Trost, Melvin *Sulfulr Ylids,* 1975 and in Block, *Reactions of Organosulfur Compounds,* 1978, pp. 91–127. Typical reaction conditions for sulfur ylid formation from a dimethylsulfoxonium salt utilizes bases such as hydroxides, metal hydrides and alkoxides in solvents such as dimethoxyethane, dimethylsufoxide and water depending on the base employed. The reactions are conducted from 0 to 20° C. preferably from 10–15° C. and preferably with alkali metal hydroxides in dimethylsulfoxide.

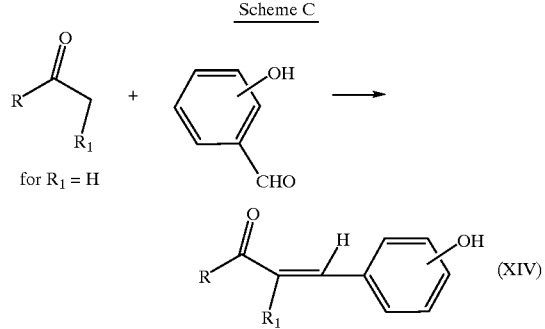

-continued

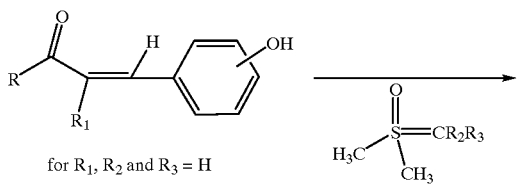

for R₁, R₂ and R₃ = H

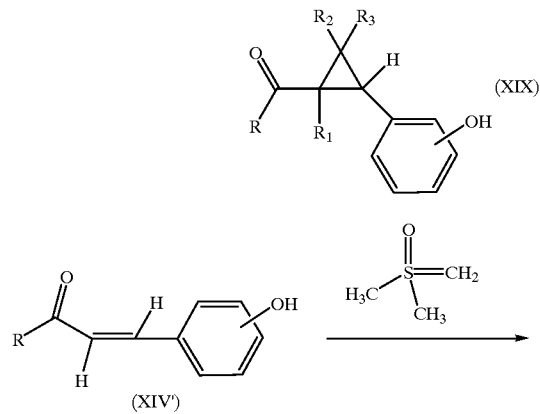

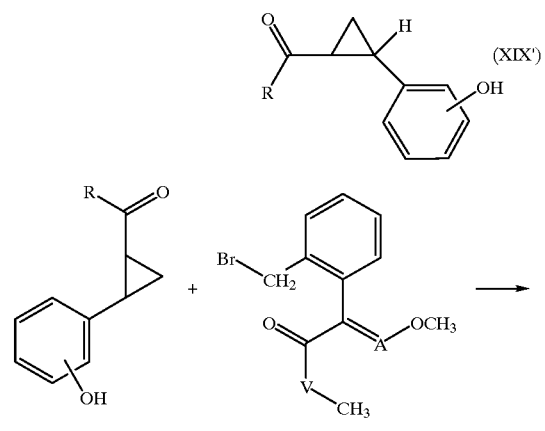

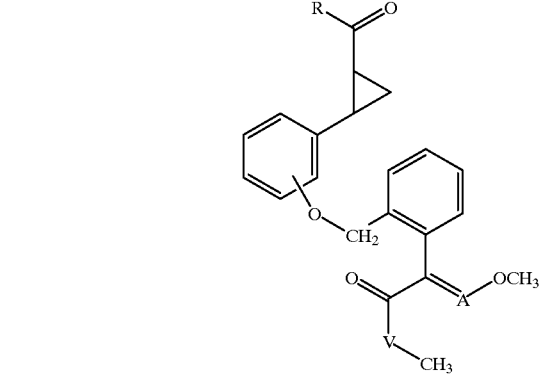

V, VI, VII

The substituted acyl cyclopropyl phenols XIX' are alkylated with the appropriate benzylbromide of Scheme A to provide compounds of Formula V,VI and VII of Tables 4, 5 and 6. and similarly the substituted acyl cyclopropyl phenols XIX provide compounds of Formula XI, XII, XIII of Tables 10, 11 and 12.

When n is 1 and m is zero the compounds of formula (I) are prepared in three step sequence shown in Scheme D. The substituted cyclopropyl phenols (XX) are prepared from α,β unsaturated compounds (XVIII) of scheme B. These enones are reacted with a sulfur ylid, prepared from a dimethylsulfoxonium salt in the presence of a base, resulting in the substituted acyl cyclopropyl phenols (XX).

Scheme D

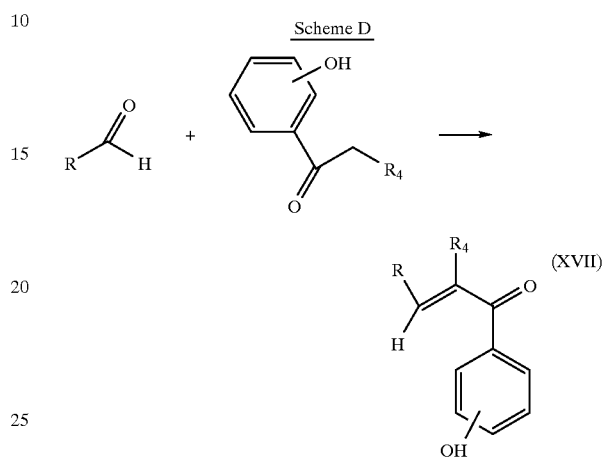

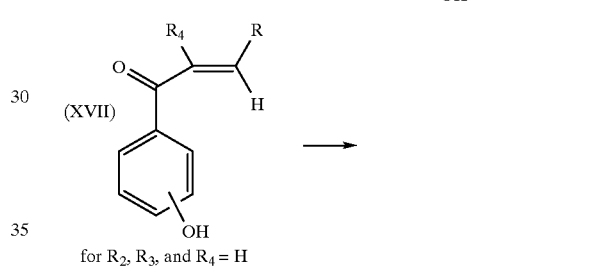

for R₂, R₃, and R₄ = H

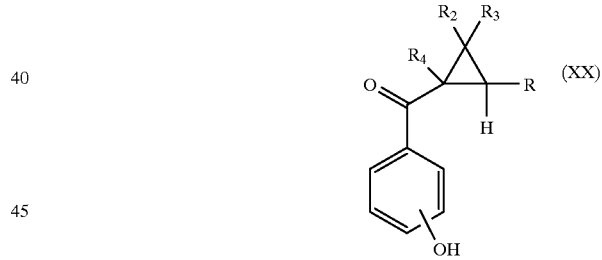

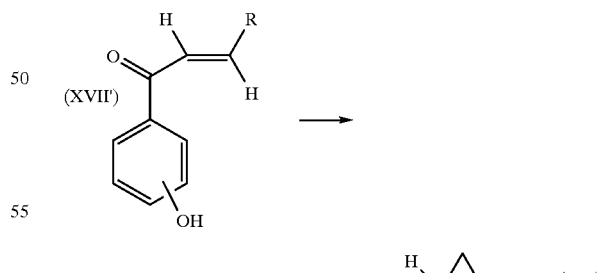

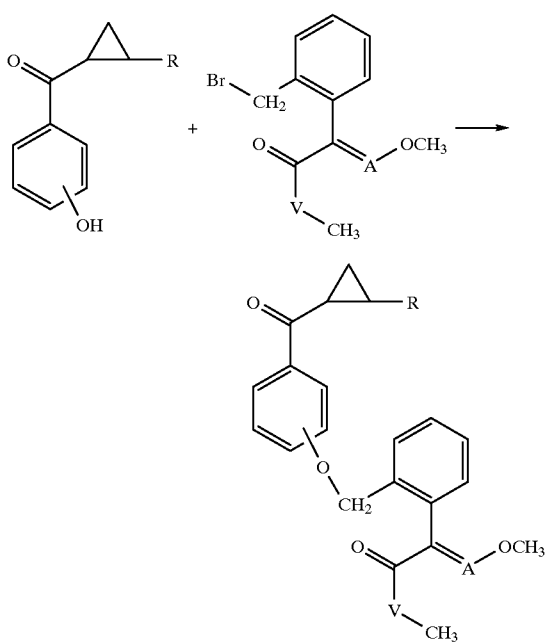

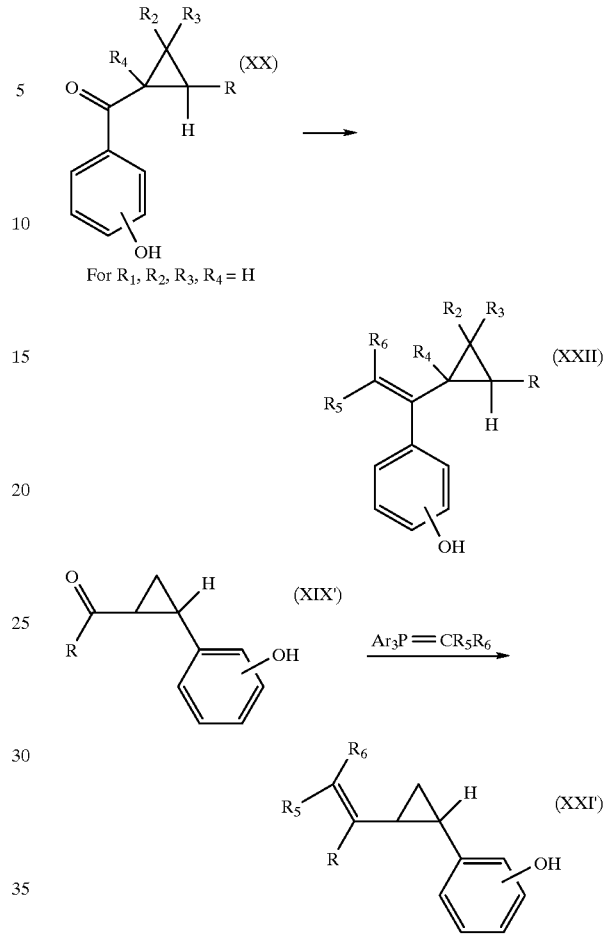

As in scheme C the substituted acyl cyclopropyl phenols XX' are alkylated with the appropriate benzylbromide of Scheme A to provide compounds of Formula VIII, IX and X of Tables 7, 8 and 9. and similarly the substituted acyl cyclopropyl phenols XX provide compounds of Formula XI, XII, XIII of Tables 10, 11 and 12.

When n and m are both zero and R is an alkenyl containing moiety the alkenyl substituted cyclopropylphenols can be prepared from intermediates XIX and XX by Wittig olefination of the acylcyclopropane phenols as shown in Scheme E where $R_5$ and $R_6$ are independently selected from hydrogen, $(C_1-C_8)$alkyl, $(C_1-C_8)$alkoxy, halo$(C_1-C_8)$alkyl, $(C_2-C_8)$alkenyl, $(C_2-C_8)$alkynyl, $(C_3-C_7)$cycloalkyl, cyano, carboxy, $(C_1-C_4)$alkoxycarbonyl, and aryl.

Scheme E

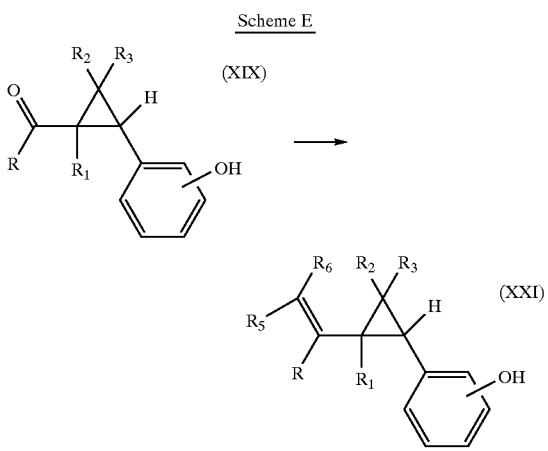

For an overview of the Wittig olefination see March, *Advanced Organic Chemistry*, 4th Ed. pp. 956–963 and references therein. For a general review of the Wittig olefination see Cadogan *Organophosphorus Reagents in Organic Synthesis*, 1979 and Johnson *Ylid Chemistry*, 1966. Typical reaction conditions for the Wittig reaction from a phosphonium salt utilizes bases such as, metal hydrides and alkoxides in solvents such as toluene, THF, ether, dimethoxyethane and ethanol depending on the base employed. The reactions are conducted from 20 to 120° C. preferably from 75 to 120° C. and preferably with alkoxides such as potassium tert-butoxide in THF. The olefinic intermediates XIX' and XXII' are alkylated with appropriate benzylbromide of Scheme A to provide compounds of Formula II, III and and IV of Tables 1, 2 and 3.

Compounds of formula (I) where $R_2$ or $R_3$ are other than hydrogen and n is 0 or 1 and m is 0 or 1 such that n+m=1 are prepared in three step sequence shown in Scheme E. The substituted cyclopropyl phenols (XXIII) and (XXIV) are prepared from α,β unsaturated compounds as described in Schemes C and D.

The substituted acyl cyclopropyl phenols XXIII and XXIV are alkylated with appropriate benzylbromide to provide compounds of Formula IX, XII and XIII of Tables 10, 11 and 12.

Compounds of formula (I) where n and m are zero and $R_1$ or $R_4$ are other than hydrogen can also be prepared as in Scheme G where $R_1$ and $R_4$ are electron withdrawing substituents such as cyano and alkoxycarbonyl. The acrylonitriles and acrylates starting materials can be prepared by conventional synthetic methods and are treated as in

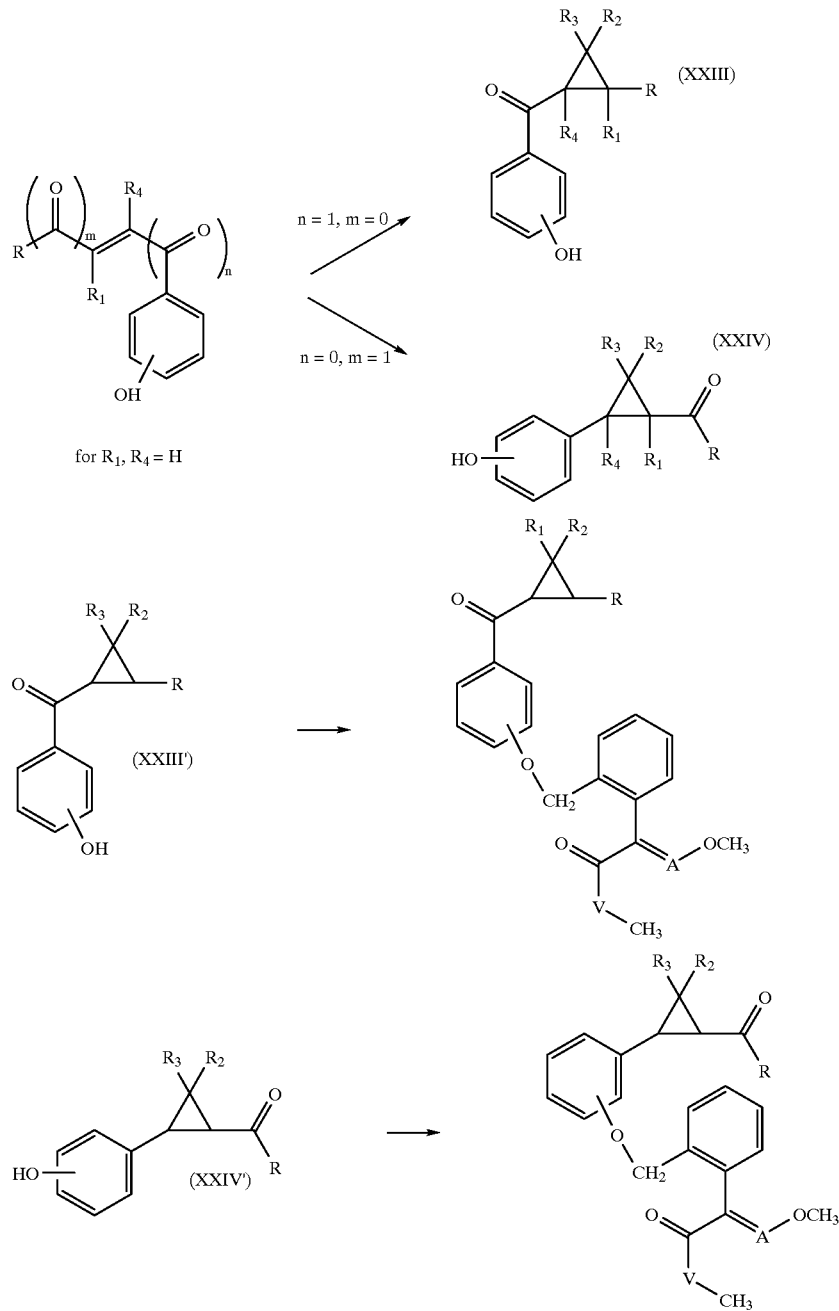

Scheme F

Schemes C and D with a sulfur ylid to provide cyclopropyl phenols XXV and XXVI as is shown in Scheme G for $R_1$ or $R_4$ as cyano. The substituted acyl cyclopropyl phenols XXV and XXVI are alkylated with the appropriate benzylbromide to provide compounds of Formula IX, XII and XIII of Tables 10, 11 and 12.

Scheme G

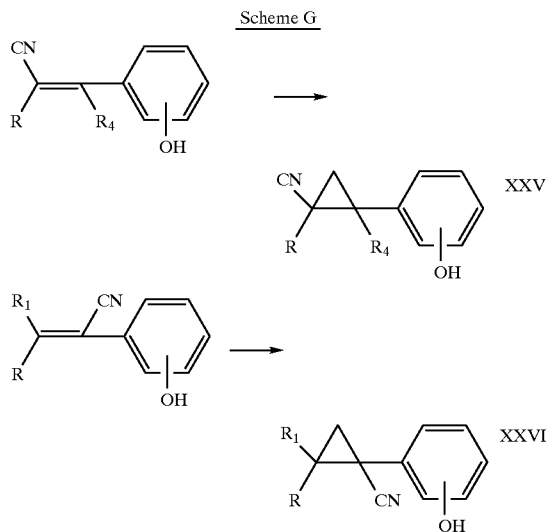

Compounds of formula (I) where n and m are zero and $R_2$ or $R_3$ are other than hydrogen can also be prepared as in Scheme H. A general overview of synthesis methods for olefins and for cyclopropanes utilizing carbenes is described in March, *Advanced Organic Chemistry*, 4th Ed, pp. 866–872 and the many references therein.

Scheme H

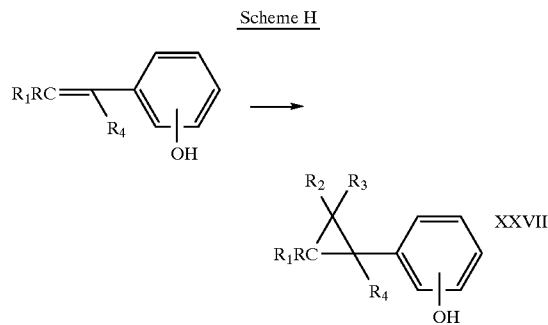

The substituted acyl cyclopropyl phenols XXVII is alkylated with the appropriate benzylbromide to provide compounds of Formula IX, XII and XIII of Tables 10, 11 and 12.

The compounds of this invention can be made according to the following procedures:

EXAMPLE 1

Methyl. 3-methoxy-2-[2-(3-(2-phenylcyclopropyl) phenoxymethyl)phenyl]propenoate (Compound 1.01, Table 1)

To a 20 ml glass vial equipped with a magnetic stirring bar was charged 1.8 g (0.0086 moles) of 1-(3-hydroxyphenyl)-2-phenyl-cyclopropane, 10 mls of dry N,N-dimethylformamide, and 0.56 g (0.0086 moles) of powdered 86% potassium hydroxide. To this solution was added 2.4 g (0.0086 moles) of methyl (E)-α-(2-(bromomethyl)phenyl)-β-methoxyacrylate in one portion. The vial was capped and stirred overnight at ambient temperature. The reaction mixture was then poured into 100 mls of water, and extracted with 3×100 mls of ethyl ether. The ether extract was then washed with 2×100 mls of water and 100 mls of saturated aqueous sodium chloride solution. The ether extract was then dried over anhydrous magnesium sulfate, filtered, and concentrated under reduced pressure with a rotary evaporator at 45° C. to afford 3.8 g of the crude product as an amber oil. This material was chromatographed on a mixed bed of neutral alumina and silica gel with 50% ethyl acetate, 50% hexane. The pure fractions were combined, and concentrated under reduced pressure with a rotary evaporator to afford 2.1 g of the title compound, Methyl 3-methoxy-2-[2-(3-(2-phenylcyclopropyl)phenoxymethyl)phenyl]propenoate as a viscous amber oil in 59% isolated yield.

1H NMR (CDCl3, tms=0 ppm) 1.4(t,2H); 2.1(m,2H); 3.6(s,3H); 3.8(s.3H); 5.0(s,2H); 6.7(m,3H); 7.0–7.4(m,9H); 7.6(m,2H)

Preparation of 1-(3-hydroxyphenyl)-2-phenylcyclopropane

To a 250 ml round bottom flask equipped with nitrogen inlet, thermometer, and reflux condenser was charged 3.5 g (0.0147 moles) of 5-(3-hydroxyphenyl)-3-phenyl-2-pyrazoline, and 4.2 g (0.1 moles) of powdered sodium hydroxide. The two solids were mixed thoroughly, then heated slowly to 250° C., under a rapid stream of nitrogen. The reaction mixture was heated continuously at 250° C. for a total of 2 hours, then cooled to ambient temperature. The resulting residue was the dissolved in 200 mls of water, then acidified to pH 2 with 1 N aqueous hydrochloric acid. The acidic solution was extracted with 3×100 mls of ethyl ether, and the ether extract was washed with 2×100 mls of water, and 100 mls of saturated aqueous sodium chloride solution. The ether extract was the dried over anhydrous magnesium sulfate, filtered and concentrated to dryness under reduced pressure with a rotary evaporator at 45° C. The resulting crude product was chromatographed on silica gel with a 15% ethyl acetate, 85% hexane mobile phase. The pure fractions were combined and concentrated under reduced pressure on a rotary evaporator to afford 1.8 g of the title compound 1-(3-hydroxyphenyl)-2-phenyl-cyclopropane as a pale yellow liquid. 58% yield.

1H NMR (CDCl3, tms=0 ppm) 1.4(t,2H); 2.2(m,2H); 5.5(s,1H); 6.5–6.8(m,3H); 7.1–7.4(m,6H)

Preparation of 5-(3-hydroxyphenyl)-3 -phenyl-2-pyrazoline

To a 250 ml round bottom flask equipped with magnetic stirrer and reflux condenser was charged 3.2 g (0.0143 moles) of 3-hydroxychalcone, 50 mls of ethanol and 0.7 g (0.0143 moles) of hydrazine monohydrate. The reaction was refluxed for a total of 2 hours, after which it was cooled to ambient temperature. The resulting solid was collected by vacuum filtration, washed with hexane, and dried in vacuuo at 40° C. overnight to afford 3.4 g of the title compound, 3-phenyl-5-(3-hydroxyphenyl)-2-pyrazoline as a tan solid. 99% isolated yield.

1H NMR (CDCl3, tms=0 ppm) 3.0(dd,1H); 3.5(dd,1H); 4.9(t,1H); 6.5–7.0(m,3H); 7.1(m,1H); 7.3–7.5(m,3H); 7.6 (m,2H); 9.0(bs,1H)

EXAMPLE 2

Methyl. 3-methoxy-2-[2-(3-(2-(thien-2-yl)cyclopropyl) phenoxymethyl)phenyl]propenoate (Compound 1.45, Table 1)

To a 20 ml glass vial equipped with a magnetic stirring bar was charged 0.5 g (0.0023 moles) of 1-(3-hydroxyphenyl)-2-(2-thienyl)cyclopropane, 10 mls of dry N,N-dimethylformamide, and 0.15 g (0.0023 moles) of powdered 86% potassium hydroxide. To this solution was added 0.66 g (0.0023 moles) of methyl (E)-α-((2-(bromomethyl)

phenyl)-β-methoxyacrylate in one portion. The vial was capped and stirred overnight at ambient temperature. The reaction mixture was then poured into 100 mls of water, and extracted with 2×100 mls of ethyl ether. The ether extract was then washed with 2×100 mls of water and 100 mls of saturated aqueous sodium chloride solution. The ether extract was then dried over anhydrous magnesium sulfate, filtered, and concentrated under reduced pressure with a rotary evaporator at 45° C. to afford 0.9 g of the crude product as an amber oil. This material was chromatographed on a mixed bed of neutral alumina and silica gel with 50% ethyl acetate, 50% hexane. The pure fractions were combined, and concentrated under reduced pressure with a rotary evaporator to afford 0.8 g of the title compound, Methyl 3-methoxy-2-[2-(3-(2-(thien-2yl)cyclopropyl) phenoxymethyl)phenyl]-propenoate as a viscous yellow oil in 97% isolated yield as a 9:1 trans:cis 1,2-cyclopropane mixture.

1H NMR (CDCl3, tms=0 ppm) 1.4(t,2H); 2.1(m,1H); 2.4(m,1H); 3.6(s,3H); 3.8(s.3H); 5.0(s,2H); 6.6(s,1H); 6.7(m,2H); 6.75(m,1H); 6.8(t,1H); 7.1(d,1H); 7.2(m,1H); 7.4(m,3H); 7.55(m,1H); 7.6(s,1H)

Preparation of 1-(3-hydroxyphenyl)-2-(2-thienyl) cyclopropane

To a 250 ml round bottom flask equipped with nitrogen inlet, thermometer, and reflux condenser was charged 5.0 g (0.0205 moles) of 3-(3-hydroxyphenyl)-5-(2-thienyl)-2-pyrazoline, and 5.0 g of powdered sodium hydroxide. The two solids were mixed thoroughly, then heated slowly to 250° C., under a rapid stream of nitrogen. The reaction mixture was heated continuously at 250° C. for a total of 2 hours, then cooled to ambient temperature. The resulting residue was the dissolved in 200 mls of water, then acidified to pH 2 with 1 N aqueous hydrochloric acid. The acidic solution was extracted with 3×100 mls of ethyl ether, and the ether extract was washed with 2×100 mls of water, and 100 mls of saturated aqueous sodium chloride solution. The ether extract was the dried over anhydrous magnesium sulfate, filtered and concentrated to dryness under reduced pressure with a rotary evaporator at 45° C. The resulting crude product was chromatographed on silica gel with a 15% ethyl acetate, 85% hexane mobile phase. The pure fractions were combined and concentrated under reduced pressure on a rotary evaporator to afford 3.6 g of the title compound 1-(3-hydroxyphenyl)-2-(2-thienyl)cyclopropane as a pale yellow liquid. 84% yield 1H NMR (CDCl3, tms=0 ppm) 1.4(t,2H); 2.2(m,1H); 2.4(m,1H); 5.0(bs,1H); 6.5–7.3(m,7H)

Preparation of 3-(3-hydroxyphenyl)-5-(2-thienyl)-2-pyrazoline

To a 250 ml round bottom flask equipped with magnetic stirrer and reflux condenser was charged 5.2 g (0.0226 moles) of 1-(3-hydroxyphenyl)-3-(2-thienyl)-3-propen-1-one in 200 mls of water and 1.1 g (0.0226 moles) of hydrazine monohydrate. The reaction was refluxed for a total of 2 hours, after which it was cooled and diluted with an additional 200 mls of water. The resulting solid was collected by vacuum filtration, washed with water and hexane, and dried in vacuuo at 40° C. overnight to afford 5.0 g of the title compound 3-(3-hydroxyphenyl)-5-(2-thienyl)-2-pyrazoline as a tan solid. 91% isolated yield.

1H NMR (CDCl3, tms=0 ppm) 3.0(dd,1 H); 3.5(dd,1H); 4.9(t, 1H); 6.4(bs,1H); 6.8(m,3H); 7.1–7.3(m,3H); 7.4(d, 1H); 9.0(bs,1H)

EXAMPLE 3

Methyl 2-[2-((3-(2-(thien-2-yl)cyclopropyl)) phenoxymethyl)phenyl]-2-methoxyiminoacetate (Compound 2.45, Table 2)

To a 20 ml glass vial equipped with a magnetic stirring bar was charged 2.2 g (0.0102 moles) of 1-(3-hydroxyphenyl)-2-(2-thienyl)cyclopropane, 15 mls of dry N,N-dimethylformamide, and 0.41 g (0.0102 moles) of powdered sodium hydroxide. To this solution was added 2.9 g (0.0102 moles) of methyl (E)-2-(bromomethyl)phenylglyoxylate O-methyloxime in one portion. The vial was capped and stirred overnight at ambient temperature. The reaction mixture was then poured into 100 mls of water, and extracted with s×100 mls of ethyl ether. The ether extract was then washed with 2×100 mls of water and 100 mls of saturated aqueous sodium chloride solution. The ether extract was then dried over anhydrous magnesium sulfate, filtered, and concentrated under reduced pressure with a rotary evaporator at 45° C. to afford 5.1 g of the crude product as an dark green oil. This material was chromatographed on a mixed bed of neutral alumina and silica gel with 50% ethyl acetate, 50% hexane. The pure fractions were combined, and concentrated under reduced pressure with a rotary evaporator to afford 3.7 g of the title compound, Methyl2-[2-((3-(2-(thien-2-yl)cyclopropyl))phenoxymethyl)phenyl]-2-methoxyiminoacetate as a viscous yellow oil. 86% isolated yield.

1H NMR (CDCl3, tms=0 ppm) 1.4(t,2H); 2.1(m,1H); 2.4(m,1H); 3.8(s,3H); 4.0(s,3H); 5.0(s,2H); 6.6–6.8(m,3H); 6.85(m,1H); 6.9(m,1H); 7.0–7.3(m,3H); 7.4–7.6(m,3H)

EXAMPLE 4

N-methyl 2-[2-((3-(2-(thien-2-yl)cyclopropyl)) phenoxymethyl)phenyl]-2-methoxyiminoacetamide (Compound 3.45, Table 3)

To a 50 ml round bottom flask equipped with magnetic stirrer and reflux condenser was charged 0.7 g (0.00166 moles) of oxime ester, 20 mls of anhydrous methanol, and 1.0 ml (0.011 moles) of 40% aqueous methyl amine. The resulting solution was refluxed for a total of 3 hours, then cooled to ambient temperature, and concentrated to dryness under reduced pressure with a rotary evaporator at 45° C. The resulting material was then chromatographed on a mixed bed of neutral alumina and silica gel with 50% ethyl acetate, 50% hexane. The pure fractions were combined, and concentrated under reduced pressure with a rotary evaporator to afford 0.5 g of the title compound, N-methyl (E)-2-[2-((3-(2-(thien-2-yl)cyclopropyl))phenoxymethyl)phenyl]-2-methoxyiminoacetamide as a viscous yellow oil. 72% isolated yield.

1H NMR (CDCl3, tms=0 ppm) 1.4(t,2H); 2.1(m,1H); 2.4(m,1H); 2.9(d,3H); 3.9(s,3H); 5.0(s,2H); 6.6–6.8(m,4H); 6.85(m,1H); 6.9(m,1H); 7.0–7.3(m,3H); 7.4–7.6(m,3H)

EXAMPLE 5

Preparation of Methyl (E)-3-methoxy-2-trans-[2-(3-(2-benzoylcyclopropyl)phenoxymethyl)-phenyl]-2-propenoate. (Compound 4.01, Table 4)

To a 20 ml glass vial equipped with a magnetic stirring bar was charged 2.4 g (0.01 moles) of 2-(3-hydroxyphenyl) cyclopropylphenylmethylketone, 10 mls of dry N,N-dimethylformamide, and 0.4 g (0.01 moles) of powdered sodium hydroxide. To this solution was added 2.8 g (0.01 moles) of methyl (E)-α-(2-(bromomethyl)phenyl)-β-methoxyacrylate in one portion. The vial was capped and stirred overnight at ambient temperature. The reaction mixture was then poured into 100 mls of water, and extracted with 3×100 mls of ethyl ether. The ether extract was then washed with 2×100 mls of water and 100 mls of saturated aqueous sodium chloride solution. The ether extract was then dried over anhydrous magnesium sulfate, filtered, and concentrated under reduced pressure with a rotary evaporator at 45° C. to afford 3.9 g of the crude product as an amber oil. This material was chromatographed on a mixed bed of neutral alumina and silica gel with 30% ethyl acetate, 70% hexane. The pure fractions were combined, and concentrated under reduced pressure with a rotary evaporator at 45° C. to afford 1.7 g of the title compound, Methyl (E)-3-methoxy-2-trans-[2-(3-(2-benzoylcyclopropyl)phenoxymethyl)-phenyl]-2-propenoate as a viscous yellow oil. 39% isolated yield.

300 MHz 1H NMR (CDCl3, tms=0 ppm) 1.5(m,1H); 1.9(m,1H); 2.6(m,1H); 2.8(m,1H); 3.7(s,3H); 3.8(s,3H); 5.0(s,2H); 6.7(s,1H); 6.75(m,2H); 7.1(m,2H); 7.3(m,2H); 7.55(m,4H); 7.6(s,1H); 8.0(m,2H)

Preparation of 2-(3-hydroxyphenyl) cyclopropylphenylmethyl ketone

To a 250 ml round bottom flask equipped with magnetic stirrer, nitrogen inlet, thermometer and addition funnel was charged 0.71 g (0.0178 moles) of 60% sodium hydroxide (oil suspension) and 50 mls of anhydrous DMSO. With stirring, under a nitrogen atmosphere, the trimethysulfoxonium iodide (3.9 g, 0.0178 moles) was added in one portion, and the reaction was stirred at ambient temperature for 30 minutes. The mixture was then cooled to 15° C., and a solution of 3-hydroxychalcone (2.0 g, 0.0089 moles) was added dropwise in 10 mls of DMSO. The reaction was stirred for 1 hour at 15° C., then allowed to warm to ambient temperature, and stirred for an additional 16 hours. The reaction mixture was the quenched with 100 mls of 0.1 N HCl, and extracted with 3×100 mls of ethyl ether. The combined ether extracts were washed successively with 2×100 mls of water, and 100 mls of saturated aqueous sodium chloride solution. The ether extract was then dried over anhydrous magnesium sulfate, filtered and concentrated to dryness under reduced pressure with a rotary evaporator at 45° C. to afford 2.1 g of the title compound, [2-(3-hydroxyphenyl)cyclopropyl]phenylmethanone, as a thick yellow oil. 100% crude yield.

300 MHz 1H NMR (CDCl3, tms=0 ppm) 1.5(m,1H); 1.9(m,1H);2.6(m,1H); 2.9(m,1H); 5.7(bs,1H); 6.8(m,3H); 7.1(t,1H); 7.4(m,2H); 7.5(d,1H); 8.0( d,2H)

EXAMPLE 6

Preparation of Methyl 3-methoxy-(E)-2-[2-trans-(3-(2-benzoylspiro[2,2]pent-1-yl)phenoxymethyl)phenyl]-2-propenoate (Compound 10.166, Table 10)

To a 20 ml glass vial equipped with a magnetic stirring bar was charged 0.5 g (0.0019 moles) of [2-(3 -hydroxyphenyl) spiro [2,2]pent-1 -yl]phenylmethyl ketone, 10 mls of dry N,N-dimethyl-formamide, and 0.076 g (0.0019 moles) of powdered sodium hydroxide. To this solution was added 0.54 g (0.0019 moles) of methyl (E)-α-(2-(bromomethyl) phenyl)-β-methoxyacrylate in one portion. The vial was capped and stirred overnight at ambient temperature. The reaction mixture was then poured into 100 mls of water, and extracted with 3×100 mls of ethyl ether. The ether extract was then washed with 2×100 mls of water and 100 mils of saturated aqueous sodium chloride solution. The ether extract was then dried over anhydrous magnesium sulfate, filtered, and concentrated under reduced pressure with a rotary evaporator at 45° C. to afford 1.1 g of the crude product as an yellow oil. This material was chromatographed on a mixed bed of neutral alumina and silica gel with 30% ethyl acetate, 70% hexane. The pure fractions were combined, and concentrated under reduced pressure with a rotary evaporator at 45° C. to afford 0.6 g of the title compound, Methyl 3-methoxy-(E)-2-[2-trans-(3-(2-benzoylspiro[2,2]pent-1-yl)phenoxymethyl)phenyl]-2-propenoate as a viscous yellow oil. 68% isolated yield.

300 MHz 1H NMR (CDCl3, tms=0 ppm) 1.0(m,2H); 1.2(m,2H); 1.3(m,2H); 3.1(m,2H); 3.7(s,3H); 3.8(s,3H); 5.0(s,3H); 6.8(m,3H); 7.2(m,2H); 7.3(m,2H); 7.4(m,4H); 7.6(s,1H); 8.0( d,2H)

Preparation of 2-(3-hydroxyphenyl)spiro[2,2]pent-1-ylphenylmethyl ketone

To a 125 ml round bottom flask equipped with magnetic stirrer, thermometer and addition funnel was charged 2.0 g (0.00637 moles) of cyclopropyldiphenyl sulfonium tetrafluoroborate and 25 mls of anhydrous DMSO. With stirring, at ambient temperature the powdered sodium hydroxide (0.25 g, 0.00637 moles) was added in one portion, and the reaction was stirred at ambient temperature for 30 minutes. The mixture was then cooled to 15° C., and a solution of 3-hydroxy chalcone (0.7 g, 0.0032 moles) was added dropwide in 10 mls of DMSO. The reaction was stirred for 1 hour at 15° C., then allowed to warm to ambient temperature, and stirred for an additional 16 hours. The reaction mixture was the quenched with 100 mls of water, and extracted with 3×100 mls of ethyl ether. The combined ether extracts were washed successively with 2×100 mls of water, and 100 mls of saturated aqueous sodium chloride solution. The ether extract was then dried over anhydrous magnesium sulfate, filtered and concentrated to dryness under reduced pressure with a rotary evaporator at 45° C. to afford 1.2 g of crude product which was chromatographed on silica gel with 30% ethyl acetate, 70% hexane. The pure fractions were combined, and concentrated under reduced pressure with a rotary evaporator at 45° C. to afford 0.5 g of the title compound, 2-(3-hydroxyphenyl)spiro[2,2]pent-1-ylphenylmethyl ketone, as a thick, pale yellow oil. 59% isolated yield.

300 MHz 1H NMR (CDCl3, tms=0 ppm) 1.0(m,2H); 1.2(m,2H); 1.3(m,2H); 3.1(s,2H); 6.0(bs,1H); 6.8(m,2H); 7.2(t,1H); 7.3(m,1H); 7.4(m,2H); 7.6( d,1H); 8.0( d,2H)

EXAMPLE 7

Preparation of Methyl. 3-methoxy-2-[2-(3-(2-(1-cyclopropylethenyl)cyclopropyl) phenoxymethyl)phenyl] propenoate Compound 1.37, Table 1)

The alkylation of 1-(3-hydroxyphenyl)-2-(1-cyclopropylethenyl)cyclopropane with methyl (E)-α-(2-(bromomethyl)phenyl)-β-methoxyacrylate is performed as in Example 6 and gave the title compound 1.37.

300 MHz 1H NMR (CDCl3, tms=0 ppm)0.5(m,2H); 0.7(m,2H); 1.1(m,1H); 1.3(m,1H); 1.4(m,1H); 1.6(m,1H); 1.9(m,1H); 3.7(s,3H); 3.8(s,3H); 4.6(d,2H); 4.95(s,2H); 6.7(m,3H); 7.2(m,2H); 7.4(m,2H); 7.5(m,1H); 7.6(s,1H)

Preparation of 1-(3-hydroxyphenyl)-2-(1-cyclopropylethenyl)cyclopropane

To a 250 ml round bottom flask equipped with magnetic stirrer, reflux condenser, and nitrogen inlet was charged 2.0 g (0.01 moles) of 2-(3-hydroxyphenyl) cyclopropylcyclopropyl ketone (3.5 g of methyltriphenyphosphonium bromide (0.01 moles), and 50 mls of anhydrous tetrahydrofuran. To this mixture was added 2.2 g ( 0.02 moles) of potassium t-butoxide, and the reaction was heated to reflux under nitrogen for a total of 3 hours. Upon cooling, the THF solution was poured into aprox. 200 ml of ethyl ether, and the organic layer was washed with 2×100 ml of water, and 100 ml of saturated aqueous sodium chloride solution. The ether extract was dried over anhydrous magnesium sulfate, filtered, and concentrated to dryness on a rotary evaporator. The crude product was chromatographed with silica gel flash chromatography using a mobile phase of 15% ethyl acetate, 85% hexane. The pure fractions were combined and concentrated on a rotary evaporator to afford 1.3 g (65% yield) of 2-(3hydroxyphenyl)-cyclopropyl cyclopropyl ketone as a pale yellow liquid.

1HNMR (300 MHz, CDCl3): 0.5(m,2H); 0.6(m,2H); 1.1 (m,1H); 1.3(m,1H); 1.4(m,1H); 1.6(m,1H); 1.9(m,1H); 4.6 (s,2H); 5.0(s,1H); 6.5(s,1H); 6.6(m,2H); 7.1(t,1H)

EXAMPLE 9

Proton NMR data (300 MHz) are provided in Table XIII for typical examples of Tables I to XII and are illustrative of the present invention.

TABLE XIII

| Compd # | |
|---|---|
| 1.01 | 1.4(t, 2H); 2.1(m, 2H); 3.6(s, 3H); 3.8(s, 3H); 5.0(s, 2H); 6.7(m, 3H); 7.0–7.4(m, 9H); 7.6(m, 2H) |
| 1.02 | 1.4(t, 2H); 2.1(m, 1H); 2.5(m, 1H); 3.6(s, 3H); 3.8(s, 3H); 5.0(s, 2H); 6.8(d, 1H); 6.9(d, 1H); 7.0–7.5(m, 11H); 7.6(s, 1H) |
| 1.03 | 1.4(t, 2H); 2.1(m, 2H); 3.6(s, 3H); 3.8(s, 3H); 5.0(s, 2H); 6.8(d, 2H); 7.0–7.4(m, 9H); 7.5(m, 1H); 7.6(s, 1H) |
| 1.04 | 1.4(t, 2H); 2.1(m, 2H); 3.6(s, 3H); 3.8(s, 3H); 5.0(s, 2H); 6.7(m, 3H); 7.0(d, 2H); 7.1–7.5(m, 6H); 7.55(m, 1H); 7.6(s, 1H) |
| 1.06 | 1.4(t, 2H); 2.1(m, 2H); 3.6(s, 3H); 3.8(s, 3H); 5.0(s, 2H); 6.8(d, 2H); 7.0–7.5(m, 8H); 7.55(m, 2H); 7.6(s, 1H) |
| 1.08 | 1.4(t, 2H); 2.1(m, 2H); 3.6(s, 3H); 3.8(s, 3H); 5.0(s, 2H); 6.7(m, 3H); 6.9–7.5(m, 8H); 7.55(m, 1H); 7.6(s, 1H) |
| 1.13 | 1.4(t, 2H); 2.1(m, 2H); 2.3(s, 3H); 3.6(s, 3H); 3.8(s, 3H); 5.0(s, 2H); 6.7(m, 3H); 7.0–7.3(m, 6H); 7.4(m, 2H); 7.55(m, 1H); 7.6(s, 1H) |
| 1.16 | 0.9(m, 2H); 1.5(m, 2H); 3.7(s, 3H); 3.9(s, 3H); 5.0(s, 2H); 6.8(m, 3H); 7.2(m, 7H); 7.5(m, 1H); 7.6(s, 1H) |
| 1.17** | 1.3(m, 2H); 1.9(t, 1H); 2.2(m, 1H); 3.6(s, 3H); 3.7(s, 3H); 4.9(s, 2H); 6.7(m, 3H); 7.0(m, 4H); 7.2(m, 2H); 7.5(m, 1H); 7.6(s, 1H) |
| 1.20 | 1.0(m, 5H); 1.3(m, 6H); 3.7(s, 3H); 3.8(s, 3H); 5.0(s, 2H); 6.8(m, 3H); 7.1(m, 2H); 7.3(m, 2H); 7.5(m, 1H); 7.6(m, 1H) |
| 1.21** | 0.6(m, 1H); 0.8(m, 2H); 0.9(m, 1H); 1.0(s, 6H); 1.6(m, 1H); 3.7(s, 3H); 3.8(s, 3H); 5.0(s, 2H); 6.6–6.8(m, 3H); 7.2(m, 2H); 7.4(m, 2H); 7.5(m, 1H); 7.6(s, 1H) |
| 1.26** | 0.9(s, 9H); 1.6(t, 2H); 2.1(m, 2H); 3.7(s, 3H); 3.8(s, 3H); 5.0(s, 2H); 6.5–6.9(m, 3H); 7.2(m, 2H); 7.4(m, 2H); 7.5(m, 1H); 7.6(s, 1H) |
| 1.27** | 0.65(m, 2H); 0.8(d, 6H); 1.3(m, 1H); 1.5(m, 1H); 3.6(s, 3H); 3.7(s, 3H); 4.9(s, 2H); 6.8(m, 3H); 7.2(m, 2H); 7.4(m, 2H); 7.5(m, 1H); 7.6(s, 1H) |
| 1.34 | 0.2(m, 2H); 0.4(d, 1H); 0.8(m, 2H); 0.9(m, 1H); 1.3(m, 2H); 1.6(m, 1H); 3.7(s, 3H); 3.8(s, 3H); 5.0(s, 2H); 6.5–6.9(m, 3H); 7.2(m, 2H); 7.4(m, 2H); 7.5(m, 1H); 7.6(m, 1H) |
| 1.45** | 1.4(t, 2H); 2.1(m, 1H); 2.4(m, 1H); 3.6(s, 3H); 3.8(s, 3H); 5.0(s, 2H); 6.6(s, 1H); 6.7(m, 2H); 6.75(m, 1H); 6.8(t, 1H); 7.1(d, 1H); 7.2(m, 1H); 7.4(m, 3H); 7.55(m, 1H); 7.6(s, 1H) |
| 1.48** | 1.3(m, 1H); 1.4(m, 1H); 2.2(m, 2H); 3.7(s, 3H); 3.9(s, 3H); 5.0(s, 2H); 6.0(m, 1H); 6.3(m, 1H); 6.8(m, 3H); 7.1(m, 2H); 7.2(s, 1H); 7.3(m, 2H); 7.5(m, 1H); 7.6(s, 1H) |
| 2.01 | 1.4(t, 2H); 2.1(m, 2H); 3.7(s, 3H); 3.9(s, 3H); 5.0(s, 2H); 6.7(m, 3H); 7.0–7.6(m, 10H) |
| 2.10 | 1.4(t, 2H); 2.1(m, 2H); 3.8(s, 3H); 4.0(s, 3H); 5.0(s, 2H); 6.7–7.6(m, 12H) |
| 2.21** | 0.6(m, 1H); 0.8(m, 2H); 0.9(m, 1H); 1.0(s, 6H); 1.5(m, 1H); 3.8(s, 3H); 4.0(s, 3H); 4.9(s, 2H); 6.7(m, 2H); 7.1(m, 2H); 7.5(m, 3H) |
| 2.34** | 0.2(m, 2H); 0.4(d, 1H); 0.8(m, 2H); 0.9(m, 1H); 1.5(m, 2H); 1.6(m, 1H); 3.8(s, 3H); 4.0(s, 3H); 5.0(s, 2H); 6.5–6.9(m, 3H); 7.1–7.4(m, 2H); 7.4–7.6(m, 3H) |
| 2.45 | 1.4(t, 2H); 2.1(m, 1H); 2.4(m, 1H); 3.8(s, 3H); 4.0(s, 3H); 5.0(s, 2H); 6.6–6.8(m, 3H); 6.85(m, 1H); 6.9(m, 1H); 7.0–7.3(m, 3H); 7.4–7.6(m, 3H) |
| 2.48** | 1.3(m, 1H); 1.4(m, 1H); 2.2(m, 2H); 3.8(s, 3H); 4.0(s, 3H); 4.9(s, 2H); 6.0(m, 1H); 6.3(m, 1H); 6.8(m, 3H); 7.2(m, 3H); 7.3(s, 1H); 7.5(t, 1H); 7.6(d, 1H) |
| 3.01 | 1.4(t, 2H); 2.2(m, 2H); 2.9(d, 3H); 3.9(s, 3H); 5.0(s, 2H); 6.7(m, 4H); 7.1–7.6(m, 9H) |
| 3.10** | 1.4(t, 2H); 2.1(m, 1H); 2.4(m, 1H); 2.9(d, 3H); 3.9(s, 3H); 5.0(s, 2H); 6.5–7.6(m, 12H) |
| 3.13 | 1.4(t, 2H); 2.1(m, 2H); 2.3(s, 3H); 2.9(d, 3H); 3.9(s, 3H); 5.0(s, 2H); 6.7(m, 3H); 7.0–7.3(m, 6H); 7.4(m, 2H); 7.55(m, 1H) |
| 3.21* | 0.6(m, 1H); 0.8(m, 2H); 0.9(m, 1H); 1.0(s, 6H); 3.0(s, 3H); 3.9(s, 3H); 5.0(s, 2H); 6.7(m, 2H); 7.1(m, 2H); 7.5(m, 3H) |
| 3.34** | 0.1(m, 2H); 0.4(d, 1H); 0.8(m, 2H); 0.9(m, 1H); 1.1(m, 1H); 1.3(m, 2H); 1.6(m, 1H); 2.9(d, 3H); 3.9(s, 3H); 4.9(s, 2H); 6.5–6.9(m, 3H); 7.2(m, 2H); 7.4(m, 2H); 7.5(m, 1H); 7.6(s, 1H) |
| 3.45 | 1.4(t, 2H); 2.1(m, 1H); 2.4(m, 1H); 2.9(d, 3H); 3.9(s, 3H); 5.0(s, 2H); 6.6–6.8(m, 4H); 6.85(m, 1H); 6.9(m, 1H); 7.0–7.3(m, 3H); 7.4–7.6(m, 3H) |
| 3.48** | 1.3(m, 1H); 1.4(m, 1H); 2.2(m, 2H); 2.9(d, 3H); 3.9(s, 3H); 5.0(s, 2H); 6.0(m, 1H); 6.3(m, 1H); 6.8(m, 3H); 7.2(m, 3H); 7.4(m, 2H); 7.5(d, 1H) |
| 4.01 | 1.5(m, 1H); 1.9(m, 1H); 2.6(m, 1H); 2.8(m, 1H); 3.7(s, 3H); 3.8(s, 3H); 5.0(s, 2H); 6.7(s, 1H); 6.75(m, 2H); 7.1(m, 2H); 7.3(m, 2H); 7.55(m, 4H); 7.6(s, 1H); 8.0(m, 2H) |
| 4.07 | 1.5(m, 1H); 1.9(m, 1H); 2.8(t, 2H); 3.7(s, 3H); 3.8(s, 3H); 5.0(s, 2H); 6.7(m, 3H); 7.2(m, 3H); 7.4(m, 5H); 7.5(m, 2H); 7.6(s, 1H) |
| 4.11 | 1.5(m, 1H); 1.9(m, 1H); 2.5(s, 3H); 2.6(m, 2H); 3.7(s, 3H); 3.8(s, 3H); 5.0(s, 2H); 6.7(m, 3H); 7.2(m, 5H); 7.3(m, 2H); 7.4(m, 1H); 7.6(s, 1H); 7.7(d, 1H) |
| 4.12 | 1.5(m, 1H); 1.9(m, 1H); 2.4(s, 3H); 2.7(m, 1H); 2.9(m, 1H); 3.7(s, 3H); 3.8(s, 3H); 5.0(s, 2H); 6.7(s, 1H); 6.8(m, 2H); 7.2(m, 2H); 7.4(m, 4H); 7.5(m, 1H); 7.6(s, 1H); 7.8(d, 2H) |
| 4.13 | 1.5(m, 1H); 1.9(m, 1H); 2.4(s, 3H); 2.6(m, 1H); 2.9(m, 1H); 3.7(s, 3H); 3.8(s, 3H); 4.9(s, 2H); 6.6(s, 1H); 6.7(m, 2H); 7.3(m, 6H); 7.5(m, 1H); 7.6(s, 1H); 7.9(d, 2H) |
| 4.14 | 1.4(m, 1H); 1.9(m, 1H); 2.6(m, 1H); 2.8(m, 1H); 3.7(s, 3H); 3.8(s, 3H); 3.9(s, 3H); 5.0(s, 2H); 6.7(s, 1H); 6.9(m, 2H); 7.0(d, 2H); 7.2(m, 2H); 7.4(m, 1H); 7.5(m, 1H); 7.6(s, 1H); 8.0(d, 2H) |
| 4.15 | 1.4(m, 1H); 1.9(m, 1H); 2.6(m, 1H); 2.9(m, 1H); 3.7(s, 3H); 3.75(s, 3H); 3.8(s, 3H); 5.0(s, 2H); 6.7(m, 3H); 7.0(m, 2H); 7.2(m, 2H); 7.3(m, 2H); 7.4(t, 1H); 7.5(m, 1H); 7.6(s, 1H) |
| 4.16 | 1.5(m, 1H); 1.9(m, 1H); 2.6(m, 1H); 2.9(m, 1H); 3.7(s, 3H); 3.8(s, 3H); 3.9(s, 3H); 5.0(s, 2H); 6.7(s, 1H); 6.8(m, 2H); 7.2(m, 3H); 7.4(m, 5H); 7.5(m, 2H); 7.6(s, 1H) |
| 4.22 | 0.9(t, 3H); 1.3(m, 3H); 1.8(m, 3H); 2.2(m, 1H); 2.5(m, 1H); 2.6(t, 2H); 3.7(s, 3H); 3.8(s, 3H); 5.0(s, 2H); 6.5(s, 1H); 6.6(m, 2H); 7.2(m, 2H); 7.4(m, 2H); 7.5(m, 1H); 7.6(m, 1H) |
| 4.24 | 0.8(d, 7H); 1.4(m, 1H); 1.8(m, 1H); 2.1(m, 1H); 2.4(d, 2H); 2.4(m, 1H); 3.7(s, 3H); 3.8(s, 3H); 5.0(s, 2H); 6.8(m, 3H); 7.1(m, 2H); 7.3(m, 2H); 7.5(m, 1H); 7.6(s 1H) |
| 4.23 | 0.8(m, 3H); 1.3(m, 7H); 1.6(m, 3H); 2.2(m, 1H); 2.4(m, 1H); 2.6(t, 2H); 3.7(s, 3H); 3.8(s, 3H); 4.9(s, 2H); 6.7(m, 3H); 7.1(m, 2H); 7.4(m, 2H); 7.5(m, 1H); 7.6(s, 1H) |
| 4.28 | 0.9(q, 3H); 1.1(dd, 3H); 1.3(m, 1H); 1.4(m, 1H); 1.5(m, 1H); 1.8(m, 1H); 2.1(m, 1H); 2.4(m, 1H); 2.7(m, 1H); 3.7(s, 3H); 3.8(s, 3H); 5.0(s, 2H); 6.7(m, 3H); 7.2(m, 2H); 7.4(m, 2H); 7.5(m, 1H); 7.6(s, 1H) |
| 4.30 | 1.3(m, 2H); 1.5(m, 1H); 1.8(m, 1H); 2.5(m, 2H); 2.7(t, 2H); 3.7(s, 3H); 3.9(s, 3H); 5.0(s, 3H); 5.1(m, 2H); 5.8(m, 1H); 6.7(m, 2H); 6.8(m, 1H); 7.2(m, 2H); 7.4(m, 2H); 7.5(m, 1H); 7.6(s, 1H) |
| 4.31 | 1.2(m, 2H); 1.4(m, 1H); 1.8(m, 1H); 1.9(m, 3H); 2.2(m, 1H); 2.4(m, 1H); 2.9(t, 2H); 3.7(s, 3H); 3.8(s, 3H); 4.7(d, 2H); 5.0(s, 2H); 6.6(s, 1H); 6.7(m, 2H); 7.2(m, 2H); 7.4(m, 2H); 7.5(m, 1H); 7.6(s, 1H) |
| 4.34 | 0.8(m, 2H); 1.0(m, 2H); 1.3(m, 1H); 1.6(m, 1H); 2.2(m, 1H); 2.4(m, 1H); 3.7(s, 3H); 3.8(s, 3H); 5.0(s, 2H); 6.6(s, 1H); 6.8(m, 2H); 7.2(m, 2H); 7.4(m, 2H); 7.5(m, 1H); 7.6(s, 1H) |
| 4.45 | 1.4(m, 1H); 1.8(m, 1H); 2.8(m, 1H); 3.7(s, 3H); 3.8(s, 3H); 5.0(s, 2H); 6.7(m, 3H); 7.1(m, 3H); 7.4(m, 2H); 7.5(m, 1H); 7.6(s, 1H); 7.7(m, 1H); 7.8(m, 1H) |
| 5.01 | 1.6(m, 1H); 1.8(m, 1H); 2.7(m, 1H); 2.9(m, 1H); 3.8(s, 3H); 4.0(s, 3H); 4.9(s, 2H); 6.7(s, 1H); 6.8(m, 2H); 7.3(m, 2H); 7.4(m, 4H); 7.6(m, 2H); 8.0(d, 2H) |
| 5.12 | 1.5(m, 1H); 1.9(m, 1H); 2.4(s, 3H); 2.6(m, 1H); 2.9(m, 1H); 3.9(s, 3H); 4.0(s, 3H); 5.0(s, 2H); 6.7(s, 1H); 6.8(m, 2H); 7.2(m, 2H); 7.4(m, 4H); 7.5(m, 1H); 7.8(d, 2H); 8.0(d, 1H) |
| 5.15 | 1.5(m, 1H); 1.9(m, 1H); 2.6(m, 1H); 2.9(m, 1H); 3.7(s, 3H); 3.8(s, 3H); 3.9(s, 3H); 5.0(s, 3H); 6.7(s, 1H); 6.8(m, 2H); 7.0(m, 2H); 7.2(m, 2H); 7.5(m, 3H); 7.6(d, 1H); 7.7(d, 1H) |
| 5.16 | 1.5(m, 1H); 1.9(m, 1H); 2.7(m, 1H); 2.9(m, 1H); 3.8(s, 3H); 3.9(s, 3H); 4.0(s, 3H); 5.0(s, 2H); 6.7(s, 1H); 6.8(m, 2H); 7.2(m, 3H); 7.4(m, 5H); 8.0(d, 1H) |

TABLE XIII-continued

| | |
|---|---|
| 5.17 | 1.6(m, 1H); 1.9(m, 1H); 2.7(m, 2H); 3.9(s, 3H); 4.0(s, 3H); 5.0(s, 2H); 6.7(s, 1H); 6.8(m, 2H); 7.2(m, 4H); 7.6(m, 4H) |
| 5.21 | 0.8(d, 7H); 1.3(m, 1H); 1.7(m, 1H); 2.1(m, 1H); 2.4(d, 2H); 2.4(m, 1H); 3.8(s, 3H); 4.0(s, 3H); 5.0(s, 2H); 6.8(m, 3H); 7.1(m, 2H); 7.4(m, 2H); 7.6(d, 1H) |
| 5.22 | 0.8(t, 3H); 1.4(m, 3H); 1.8(m, 3H); 2.2(m, 1H); 2.5(m, 1H); 2.6(t, 2H); 3.8(s, 3H); 4.0(s, 3H); 5.0(s, 2H); 6.6(s, 1H); 6.7(m, 2H); 7.2(m, 2H); 7.4(m, 2H); 7.5(d, 1H) |
| 5.28 | 0.9(t, 3H); 1.1(d, 3H); 1.3(m, 1H); 1.5(m, 1H); 1.8(m, 2H); 2.2(m, 1H); 2.4(m, 1H); 2.6(q, 1H); 3.8(s, 3H); 4.0(s, 3H); 5.0(s, 2H); 6.6(s, 1H); 6.7(m, 2H); 7.2(m, 2H); 7.4(m, 2H); 7.5(d, 1H) |
| 5.30 | 1.3(m, 1H); 1.7(m, 1H); 2.2(m, 1H); 2.4(m, 2H); 2.5(m, 1H); 2.7(t, 2H); 3.7(s, 3H); 4.0(s, 3H); 4.9(s, 2H); 5.0(m, 2H); 5.7(m, 1H); 6.5(s, 1H); 6.6(m, 2H); 7.2(m, 2H); 7.4(m, 2H); 7.5(m, 1H); 7.6(s, 1H); 7.9(d, 2H) |
| 5.31 | 1.4(m, 1H); 1.6(m, 1H); 1.8(s, 3H); 2.2(m, 1H); 2.4(t, 2H); 2.5(m, 1H); 2.8(t, 2H); 3.8(s, 3H); 4.0(s, 3H); 4.7(d, 2H); 5.0(s, 2H); 6.6(s, 1H); 6.7(m, 2H); 7.2(m, 2H); 7.4(m, 2H); 7.5(d, 1H) |
| 5.34 | 0.9(m, 2H); 1.1(m, 2H); 1.3(m, 1H); 1.7(m, 1H); 2.1(m, 1H); 2.3(m, 1H); 2.4(m, 1H); 3.8(s, 3H); 4.0(s, 3H); 5.0(s, 2H); 6.7(s, 1H); 6.8(m, 2H); 7.2(m, 2H); 7.4(m, 2H); 7.5(d, 1H) |
| 6.01 | 1.5(m, 1H); 1.8(m, 1H); 2.7(m, 1H); 2.9(s, 4H); 4.0(s, 3H); 5.0(s, 2H); 6.7(m, 3H); 7.2(m, 2H); 7.5(m, 6H); 8.0(d, 2H) |
| 6.07 | 1.5(m, 1H); 1.9(m, 1H); 2.8(t, 2H); 2.9(d, 3H); 4.0(s, 3H); 5.0(s, 2H); 6.7(m, 4H); 7.1(m, 3H); 7.4(m, 4H); 7.5(d, 1H) |
| 6.11 | 1.5(m, 1H); 1.6(m, 3H); 1.9(m, 1H); 2.7(m, 2H); 2.9(d, 3H); 4.0(s, 3H); 5.0(s, 2H); 6.7(m, 4H); 7.2(m, 4H); 7.4(m, 3H); 7.4(m, 1H); 7.5(d, 1H) |
| 6.12 | 1.4(m, 1H); 1.8(m, 1H); 2.3(s, 3H); 2.6(m, 1H); 2.8(d, 3H); 2.9(m, 1H); 3.9(s, 3H); 5.0(s, 2H); 6.6(s, 1H); 6.7(m, 2H); 7.2(m, 2H); 7.4(m, 4H); 7.5(d, 1H); 7.6(d, 2H) |
| 6.15 | 1.4(m, 1H); 1.8(m, 1H); 2.5(m, 1H); 2.7(d, 3H); 2.9(m, 1H); 3.6(s, 3H); 3.8(s, 3H); 4.9(s, 2H); 6.7(m, 3H); 6.9(m, 2H); 7.2(m, 2H); 7.4(m, 3H); 7.5(d, 1H); 7.6(d, 1H) |
| 6.16 | 1.5(m, 1H); 1.9(m, 1H); 2.6(m, 1H); 2.8(m, 1H); 2.9(d, 3H); 3.9(s, 3H); 4.0(s, 3H); 5.0(s, 2H); 6.7(s, 1H); 6.8(m, 2H); 7.2(m, 4H); 7.6(m, 5H); 8.0(t, 1H) |
| 6.17 | 1.6(m, 1H); 1.9(m, 1H); 2.8(m, 2H); 3.0(d, 3H); 4.0(s, 3H); 5.0(s, 2H); 6.7(s, 1H); 6.8(m, 2H); 7.2(m, 3H); 7.5(m, 5H) |
| 6.22 | 0.9(t, 3H); 1.4(m, 2H); 1.8(m, 2H); 2.2(m, 1H); 2.5(m, 1H); 2.6(t, 2H); 2.9(d, 3H); 4.0(s, 3H); 5.0(s, 2H); 6.6(s, 1H); 6.7(m, 2H); 7.2(m, 2H); 7.4(m, 2H); 7.5(d, 1H) |
| 6.24 | 0.9(d, 7H); 1.3(m, 1H); 1.7(m, 1H); 2.1(m, 1H); 2.4(d, 2H); 2.9(d, 3H); 3.9(s, 3H); 4.9(s, 2H); 6.5(s, 1H); 6.6(m, 3H); 7.1(m, 2H); 7.4(m, 2H); 7.5(d, 1H) |
| 6.28 | 0.8(t, 3H); 1.1(d, 3H); 1.3(m, 1H); 1.5(m, 1H); 1.8(m, 2H); 2.2(m, 1H); 2.4(m, 1H); 2.6(q, 1H); 3.0(d, 3H); 4.0(s, 3H); 5.0(s, 2H); 6.6(s, 1H); 6.7(m, 2H); 7.2(m, 2H); 7.4(m, 2H); 7.5(d, 1H) |
| 6.31 | 1.4(m, 1H); 1.7(m, 1H); 1.8(s, 3H); 2.2(m, 1H); 2.4(t, 1H); 2.5(m, 1H); 2.8(t, 2H); 2.9(d, 3H); 4.0(s, 3H); 4.7(d, 2H); 5.0(s, 2H); 6.6(s, 1H); 6.7(m, 2H); 7.2(m, 2H); 7.4(m, 2H); 7.5(m, 1H) |
| 6.34 | 0.9(m, 2H); 1.1(m, 2H); 1.3(m, 1H); 1.7(m, 1H); 2.1(m, 1H); 2.3(m, 1H); 2.5(m, 1H); 2.9(d, 3H); 4.0(s, 3H); 5.0(s, 2H); 6.6(s, 1H); 6.7(m, 2H); 7.2(m, 2H); 7.5(m, 2H); 7.6(d, 1H) |
| 7.01 | 1.3(m, 2H); 1.7(m, 2H); 3.7(s, 3H); 3.85(s, 3H); 4.95(s, 2H); 6.8(d, 2H); 7.2(m, 3H); 7.4(m, 2H); 7.5(m, 1H); 7.6(s, 1H) |
| 10.59 | 1.4(m, 2H); 1.7(m, 2H); 3.7(s, 3H); 3.85(s, 3H); 4.9(s, 2H); 6.8(m, 3H); 7.2(m, 2H); 7.4(m, 2H); 7.5(m, 1H); 7.6(s, 1H) |
| 10.61 | 1.3(m, 2H); 1.7(m, 2H); 3.7(s, 3H); 3.85(s, 3H); 4.95(s, 2H); 6.8(d, 2H); 7.2(m, 3H); 7.4(m, 2H); 7.5(m, 1H); 7.6(s, 1H) |
| 10.127 | 1.3(t, 3H); 3.2(m, 1H); 3.3(m, 1H); 3.5(m, 1H); 3.7(s, 3H); 3.8(s, 3H); 4.2(q, 2H); 4.9(s, 3H); 6.6(d, 1H); 6.7(m, 2H); 7.1(t, 1H); 7.2(m, 2H); 7.3(m, 2H); 7.4(m, 2H); 7.5(m, 1H); 7.6(s, 1H); 7.9(d, 2H) |
| 10.166 | 1.0(m, 2H); 1.2(m, 2H); 1.3(m, 2H); 3.1(m, 2H); 3.7(s, 3H); 3.8(s, 3H); 5.0(s, 3H); 6.8(m, 3H); 7.2(m, 2H); 7.3(m, 2H); 7.4(m, 4H); 7.6(s, 1H); 8.0(d, 2H) |
| 11.59 | 1.4(m, 2H); 1.7(m, 2H); 3.8(s, 3H); 3.95(s, 3H); 4.9(s, 2H); 6.8(m, 3H); 7.2(m, 2H); 7.5(m, 3H) |
| 12.59 | 1.4(m, 2H); 1.7(m, 2H); 2.9(d, 3H); 3.95(s, 3H); 4.9(s, 2H); 6.8(m, 4H); 7.2(m, 2H); 7.5(m, 3H) |

*NMR at 200 MHz
**The isomer mixture as determined by proton NMR, for the stereochemistry of the 1,2-cyclopropane substituents, for the following compounds are:

| Compound # | Trans | Cis |
|---|---|---|
| 1.17 | 2 | 1 |
| 1.20 | 6 | 1 |
| 1.21 | 7 | 3 |
| 1.26 | 7 | 3 |
| 1.27 | 2 | 1 |
| 1.45 | 9 | 1 |
| 1.48 | 6 | 1 |
| 2.21 | 7 | 3 |
| 2.34 | 3 | 2 |
| 2.48 | 7 | 3 |
| 3.10 | 3 | 2 |
| 3.34 | 3 | 2 |
| 3.48 | 10 | 1 |

EXAMPLE 9

Numerous compounds of this invention were tested for fungicidal activity in vivo against the diseases described below. The compounds were dissolved in a 2:1:1 mixture of water, acetone and methanol (by volume), sprayed onto the plants, allowed to dry (two hours) and then the plants were inoculated with fungal spores. Each test utilized control plants which were sprayed with the water, acetone and methanol mixture and inoculated. The remainder of the technique of each of the tests is given below along with the results for various compounds described herein by the Compound # against the various fungi at a dose of 300 grams per hectare. The results are reported as percent disease control, compared to the control wherein one hundred was rated as total disease control and zero as no disease control. The application of the fungi to the test plants was as follows:

Wheat Leaf Rust (WLR)

*Puccinia recondita* (f. sp. *tritici*) was cultured on 7 day old wheat (cultivar Fielder) over a 12 day period in the greenhouse. Spores were collected from the leaves by settling on aluminum foil. The spores were cleaned by sieving through a 250 micron opening screen and stored or used fresh. Storage employed sealed bags in an Ultralow freezer. A spore suspension was prepared from dry uredia by adding 20 mg (9.5 million spores) per mL of Soltrol oil. The suspension was dispensed into gelatin capsules (0.7 mL capacity) which attach to the oil atomizers. One capsule is used per flat of twenty 2 inch square pots of 7 day old Fielder wheat. After waiting for at least 15 minutes for the oil to evaporate from the wheat leaves, the plants were placed in a dark mist chamber (18–20° C. and 100% relative humidity) for 24 hours. The plants were then put in the greenhouse for the latent period and scored after 12 days for disease levels. For protective tests the plants are inoculated one day after spraying the plants with the fuingicide compounds.

Wheat Leaf Blotch (SNW)

Cultures of *Septoria nodorzim* was maintained on Czapek-Dox V-8 juice agar plates in an incubator at 20° C. with alternating periods of 12 hours of light and 12 hours of darkness for 3 weeks. A water suspension of the spores was obtained by shaking the portion of the plate with fungal material in deionized water and filtering through cheesecloth. The spore-containing water suspension was diluted to a spore concentration of $3.0 \times 10^6$ spores per ml. The inoculum was dispersed by a DeVilbiss atomizer over one week old Fielder wheat plants which had been previously sprayed with the fungicide compound. The inoculated plants were placed in a humidity cabinet at 20° C. with alternating 12 hours of light and 12 hours of darkness for 7 days. The inoculated seedlings were then moved to a controlled environment room at 20° C. for 2 days of incubation. Disease control values were recorded as percent control.

Wheat Powdery Mildew (WPM)

*Erysiphe graminis* (f. sp. *tritici*) was cultured on wheat seedlings in a controlled temperature room at 18° C. Mildew spores were shaken from the culture plants onto 7 day old wheat seedlings which had been previously sprayed with the fungicide compound. The inoculated seedlings were kept in a controlled temperature room at 18° C. and subirrigated. The percent disease control was rated 7 days after the inoculation.

Cucumber Powdery Mildew (CPM)

*Sphaerotheca fulginea* was maintained on cucumber plants, cv. Bush Champion, in the greenhouse. Inoculum was prepared by washing the spores from the leaves with water which had 1 drop of Tween 80 per 100 ml. After shaking the plants, the inoculum was filtered through cheese cloth and misted onto the plants with a squirt bottle mister. The spore count was 100,000 spores/ml. The plants were then placed in the greenhouse for infection and incubation. The plants were scored seven days after inoculation. Disease control values were recorded as percent control.

Tomato Late Blight (TLB)

Cultures of *Phytophthora infestans* were maintained on green pea-amended agar for two to three to four weeks. The spores were washed from the agar with water and dispersed by DeVilbiss atomizer over the leaves of 3-week old Pixie tomato plants which had been sprayed previously with experimental fungicides. The inoculated plants were placed in a humidity cabinet at 20° C. for 24 hours for infection. The plants were then removed to a controlled environment room at 20° C. The plants were scored for disease control after five days.

Grape Downy Mildew (GDM)

*Plasmopara viticola* was maintained on leaves of live grape plants, cv. Delaware, in a controlled temperature chamber at 20° C. in humid air with moderate light intensity for 7 to 8 days. A water suspension of the spores from infested leaves was obtained and the spore concentration was adjusted to about $3 \times 10^5$ per ml of water. Delaware grape plants were inoculated by spraying the underside of leaves with a DeVilbiss atomizer until small drops were observed on the leaves. The inoculated plants were incubated in a mist chamber for 24 hours at 20° C. The plants were then removed to a controlled environmental room at 20° C. Disease control values were recorded as percent control seven days after inoculation.

When tested against cucumber powdery mildew at a dose of 300 grams per hectare, compounds 1.01, 1.03, 1.04, 1.08, 1.16, 1.20, 1.37, 1.38, 2.20, 2.21, 2.34, 3.01, 3.10, 3.20, 3.34, 4.24, 5.62 and 10.61 exhibited 100% control.

When tested against *Septoria nodorum* at 300 grams per hectare compounds 1.01, 1.04, 1.13, 1.20, 1.21, 1.37, 1.38, 2.20, 2.21, 3.01, 3.10, 3.13, 3.20, 3.21, 3.34, 3.45, 5.62, and 10.166 exhibited 95% or better control.

When tested against wheat leaf rust at 300 grams per hectare compounds 1.01, 1.03, 1.08, 1.19, 1.20, 1.21, 1.27, 1.34, 2.20, 2.21, 2.34, 3.01, 3.10, 3.13, 3.20, 3.21, 3.34, 3.45, 4.01, 4.11, 4.14, 4.16, 4.23, 4.28, 4.34, 4.45, 4.62, 5.01, 5.62, 6.01, 6.07, 6.11, 6.12, 6.15, 6.16, 6.17, 7.01, 10.74 and 10.98 exhibited 100% control.

When tested against wheat powdery mildew at 300 grams per hectare compounds 1.03, 1.08, 1.19, 1.20, 1.21, 1.27, 1.37, 2.20, 2.21, 2.34, 3.20, and 3.45 exhibited 99% or better control.

When tested against grape downy mildew at 300 grams/hectare compounds 1.01, 1.03, 1.04, 1.06, 1.08, 1.19, 1.20, 1.21, 1.26, 1.27, 1.34, 1.37, 1.38, 1.39, 2.20, 2.21, 2.34, 3.01, 3.10, 3.13, 3.20, 3.21, 3.34, 4.13, 4.23, 4.28, 4.34 and 10.166 exhibited 100% control.

When tested against tomato late blight at 300 grams/hectare compounds 1.01, 1.03, 1.04, 1.20, 1.34, 1.45, 2.20, 3.01, 3.10, 3.20, 3.21, 3.34, 3.45, 4.04, 4.22, 4.24, 4.28, 4.30, 4.34, 4.62, 5.04, 5.22, 5.34, 5.38, 5.62, 6.04, 6.22, 6.24, 6.28, 6.34, 6.38, 10.01 and 12.01 exhibited 95% or better control.

The compounds of this invention are useful as agricultural fungicides and, as such, can be applied to various loci such as the seed, the soil or the foliage.

The compounds of this invention can be applied as fungicidal sprays by methods commonly employed, such as conventional high-volume hydraulic sprays, low-volume sprays, air-blast spray, aerial sprays and dusts. The dilution and rate of application will depend upon the type of equipment employed, the method of application, plants to be treated and diseases to be controlled. Generally, the compounds of this invention will be applied in amount of from about 0.005 kilogram to about 50 kilograms per hectare and preferably from about 0.025 to about 25 kilograms per hectare of the active ingredient.

As a seed protectant, the amount of toxicant coated on the seed is usually at a dosage rate of from about 0.05 to about 20, preferably from about 0.05 to about 4, and more preferably from about 0.1 to about 1 grams per hundred kilograms of seed. As a soil fungicide the chemical can be incorporated in the soil or applied to the surface usually at a rate of from about 0.02 to about 20, preferably from about 0.05 to about 10, and more preferably from about 0.1 to about 5 kilograms per hectare. As a foliar fungicide, the toxicant is usually applied to growing plants at a rate of from about 0.01 to about 10, preferably from about 0.02 to 5, and more preferably from about 0.25 to about 1 kilograms per hectare.

Inasmuch as the compounds of this invention display fungicidal activity, these compounds can be combined with other known fungicides to provide broad spectrum activity. Suitable fungicides include, but are not limited to, those compounds listed in U.S. Pat. No. 5,252,594 (see in particular columns 14 and 15).

The compounds of this invention can be advantageously employed in various ways. Since these compounds possess broad spectrum fungicidal activity, they can be employed in the storage of cereal grain. These compounds can also be employed as fungicides in cereals including wheat, barley and rye, in rice, peanuts, beans and grapes, on turf, in fruit, nut and vegetable orchards, and for golf course applications.

Examples of diseases against which the compounds of the invention are useful include helminthosporium of corn and barley, wheat and barley powdery mildew, wheat leaf and stem rusts, tomato early blight, tomato late blight, peanut early leaf spot, grape powdery mildew, grape black rot, apple scab, apple powdery mildew, cucumber powdery mildew, brown rot of fruits, botrytis, bean powdery mildew, cucumber anthracnose, *Septoria nodurum* of wheat, rice sheath blight and rice blast.

EXAMPLE 10

Numerous compounds of this invention were tested for insecticidal activity in vivo against the insects described below. The following test method was used to evaluate compounds of the present invention for insecticidal activity. The compound to be evaluated was dissolved in an appropriate solvent, usually a mix of acetone, methanol and water, and sprayed over three excised leaf disks using a flat fan nozzle. After spraying, the leaf disks were allowed to dry. Two disks were infested with the leaf chewing insects (southern armyworm and Mexican bean beetle) and the third leaf disk was already infested with the two-spotted spider mite prior to spraying. The tested insect species were:

| AW | southern armyworm | *Spodoptera eridamia* |
|---|---|---|
| BB | Mexican bean beetle | *Epilachna varivestis* |
| MTA | two-spotted spider mite | *Teranychus uricate* |

Observations as percent control were made by visual inspection 24–48 hours after spraying.

When tested against southern army worm at 600 grams/hectare compounds 1.04, 1.08, 1,16, 1.27, 1.34, 2,21, 3.20*, 3.21, 4.01, 4.62*, and 5.62* provided 75% or better control.
*tested at 300 grams/hectare When tested against Mexican bean beetle at 300 grams/hectare compounds 1.01, 1.02, 1.04, 1.06, 1.13, 1.16, 1.19, 1.20, 1.21, 1.26, 1.27, 1.34, 1.45, 2.10, 2.21, 2.34, 3.21, 3.34, 4.01, 4.04, 4.07, 4.12, 4.13, 4.15, 4.20, 4.22, 4.23, 4.28, 4.32, 4.34, 4.45, 4.62, 5.21, 5.62, 6.04, 10.74, 10.98 and 10.166 provided 100% control.

When tested against two-spotted spider mite at 300 grams/hectare compounds 1.01, 1.03, 1.04, 1.06, 1.13, 1.16, 1.19, 1.20, 1.21, 1.26, 1.27, 1.34, 1.45, 2.21, 2.34, 3.20, 3.21, 3.34, 4.04, 4.20, 4.22, 4.23, 4.28, 4.62, 5.62, 6.04, 10.01, 10.16, 10.59, 10.74, and 10.98 provided 100% control.

The compositions and compounds of this invention can be applied directly to the locus to be protected, as for example, the area around or upon economic plants infected with insects or to plants on which infestation is to be prevented. Examples of injurious insects belong to the orders Lepidoptera, Coleoptera, Diptera, Thysanoptera, Hymenoptera, Heteroptera, Homoptera, Orthoptera, and Acarina. The compounds and compositions may be used either as contact or systemic pesticides. The compounds of the invention are applied to the insect's habitat at a rate of 0.0005 to 10 kilograms per hectare, preferably 0.05 to 5 and most preferably from 0.1 to 1 kilogram per hectare.

In the practice of the method of the invention, the active compound may be applied to the soil or foliage where it is absorbed by the plant, translocated to other plant parts and ultimately ingested by the pest or insects by means of ingestion of the plant part(s). This means of application is referred to as systemic application. Alternatively, the active compound may be applied to the soil and contacted therein with the insects and other pests to be controlled. This means of application is referred to as soil application. In another alternative, the active compound may be foliarly applied to the plants to be freed from insects and other pests which feed on the foliage.

Compositions and formulations according to the present invention may also include known pesticidal compounds. This expands the spectrum of activity of the preparation and may give rise to synergism. Suitable insecticides known in the art include those listed in U.S. Pat. No. 5,075,471, see in particular columns 14 and 15.

The compounds of the present invention can be used in the form of compositions or formulations. Examples of the preparation of compositions and formulations can be found in the American Chemical Society publication "Pesticidal Formulation Research," (1969), Advances in Chemistry Series No. 86, written by Wade Van Valkenburg; and the Marcel Dekker, Inc. publication "Pesticide Formulations", (1973) edited by Wade Van Valkenburg. In these compositions and formulations, the active substance is mixed with conventional inert agronomically acceptable (i.e., plant compatible and/or pesticidally inert) pesticide diluents or extenders such as solid carrier material or liquid carrier material, of the type usable in conventional pesticide compositions or formulations. By "agronomically acceptable carrier is meant any substance which can be used to dissolve, disperse of diffuse the active ingredient in the composition without impairing the active ingredients effectiveness and which by itself has no significant detrimental effect on the soil, equipment, desirable plants, or agronomic environment. If desired, adjuvants such as surfactants, stabilizers, antifoam agents and antidrift agents may also be combined.

Examples of compositions and formulations according to the invention are aqueous solutions and dispersions, oily solutions and oil dispersions, pastes, dusting powders, wettable powders, emulsifiable concentrates, flowables, granules, baits, invert emulsions, aerosol compositions and fumigating candles. Wettable powders, pastes, flowables and emulsifiable concentrates are concentrated preparations which are diluted with water before or during use. In such formulations, the compounds are extended with a liquid or solid carrier and, when desired, suitable surfactants are incorporated. Baits are preparations generally comprising a food or other substance attractive to insects, that includes at least one compound of the instant invention.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art, and a discussion of adjuvants can be found in many references, such as in the John W. McCutcheon, Inc. publication "Detergents and Emulsifiers, Annual."

The active compounds of the present invention may be employed alone or in the form of mixtures with one another and/or with such solid and/or liquid dispersible carrier vehicles and/or with other known compatible active agents, especially plant protection agents, such as other insecticides, arthropodicides, nematicides, fungicides, bactericides, rodenticides, herbicides, fertilizers, growth-regulating agents, synergists.

In the compositions of the invention, the active compound is present in an amount substantially between about 0.0001–99% by weight. For compositions suitable for storage or transportation, the amount of active ingredient is preferably between about 0.5–90% by weight, and more preferably between about 1–75% by weight of the mixture. Compositions suitable for direct application or field application generally contain the active compound in an amount substantially between about 0.0001–95%, preferably between about 0.0005–90% by weight, and more preferably between about 0.001–75% by weight of the mixture. The composition can also be stated as a ratio of the compound to the carrier. In the present invention the weight ratio of these materials (active compound/carrier) can vary from 99:1 to 1:4 and more preferably from 10:1 to 1:3.

In general, the compounds of this invention can be dissolved in certain solvents such as acetone, methanol, ethanol, dimethylformamide, pyridine or dimethyl sulfoxide and such solutions can be diluted with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent to enhance dispersion of the compound in water. The concentration of the active ingredient in emulsifiable concentrates is usually from about 10% to about 90%, and in flowable emulsion concentrates, can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of from about 20% to about 99%, preferably from about 40% to about 75%. A typical wettable powder is made by blending 50 parts of a pyridazinone, 45 parts of a synthetic precipitated hydrated silicon dioxide, such as that sold under the trademark Hi-SilR®, and 5 parts of sodium lignosulfonate. In another preparation a kaolin type (Barden) clay is used in place of the Hi-Sil in the above wettable powder, and in another such preparation 25% of the Hi-Sil is replaced with a synthetic sodium silicoaluminate sold under the trademark Zeolex®7.

Dusts are prepared by mixing the pyridazinone, or the enantiomorphs, salts and complexes thereof with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted to from about 1% to about 10% use concentration.

The active compounds can be applied as insecticide sprays by methods commonly employed, such as conventional high-gallonage hydraulic sprays, low gallonage sprays, ultra-low-volume sprays, airblast spray, aerial sprays, and dusts.

The present invention also contemplates methods of killing, combating or controlling pests which compromises contacting pests with a combative or toxic amount (i.e. a pesticidally effective amount) of at least one active compound of the invention alone or together with a carrier vehicle (composition or formulation) as noted above. The term "contacting" as employed in the specification and claims means applying to at least one of (a) such pests and (b) the corresponding habit at thereof (i.e., the locus to be protected, for example, to a growing crop or to an area where a crop is to be grown) the active compound of this invention alone or as a constituent of a composition or formulation.

In addition to the aforementioned ingredients the preparations according to the invention may also contain other substances commonly used in preparations of this kind. For example, a lubricant, such as calcium stearate or magnesium stearate, may be added to a wettable powder or to a mixture to be granulated. Furthermore there may, for example, be added "adhesives" such as polyvinylalcohol-cellulose derivatives or other colloidal materials, such as casein, to improve the adherence of the pesticide to the surface to be protected.

We claim:

1. A compound of the formula:

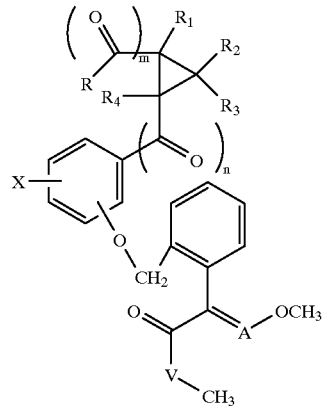

wherein A is N or CH; V is O or NH;

m and n are the integers 0 and 1, provided that m+n is 0 or 1;

X is independently selected from hydrogen, halo, $(C_1-C_4)$ alkyl, and $(C_1-C_4)$alkoxy;

R is selected from hydrogen, $(C_1-C_{12})$alkyl, $(C_1-C_{12})$ alkoxy, halo$(C_1-C_{12})$alkyl, $(C_2-C_{12})$alkenyl, $(C_2-C_{12})$ alkynyl, $(C_1-C_{12})$alkoxy$(C_1-C_{12})$alkyl, $(C_3-C_7)$ cycloalkyl, halo$(C_3-C_7)$cycloalkyl, $(C_3-C_7)$cycloalkyl $(C_1-C_{12})$alkyl, $(C_3-C_7)$cycloalkyl$(C_2-C_{12})$alkenyl, $(C_3-C_7)$cycloalkyl$(C_2-C_{12})$alkynyl, $(C_1-C_{12})$alkyl $(C_3-C_7)$cycloalkyl, $(C_1-C_{12})$alkoxy$(C_3-C_7)$cycloalkyl, $(C_1-C_{12})$alkoxy$(C_1-C_{12})$alkyl$(C_3-C_7)$cycloalkyl, $(C_2-C_{12})$alkenyl$(C_3-C_7)$cycloalkyl, $(C_2-C_{12})$alkynyl $(C_3-C_7)$cycloalkyl, halo$(C_1-C_{12})$alkyl$(C_3-C_7)$ cycloalkyl, $(C_1-C_{12})$alkoxy$(C_2-C_{12})$alkenyl$(C_3-C_7)$ cycloalkyl, $(C_1-C_{12})$alkoxy$(C_2-C_{12})$alkynyl$(C_3-C_7)$ cycloalkyl, $(C_3-C_7)$cycloalkyl$(C_3-C_7)$cycloalkyl, $(C_1-C_{12})$alkly$(C_3-C_7)$cycloalkyl$(C_3-C_7)$cycloalkyl, $(C_2-C_{12})$alkenyl$(C_3-C_7)$cycloalkyl$(C_3-C_7)$cycloalkyl, $(C_2-C_{12})$alkynyl$(C_3-C_7)$cycloalkyl$(C_3-C_7)$cycloalkyl, $(C_3-C_7)$cycloalkyl$(C_1-C_{12})$alkyl$(C_3-C_7)$cycloalkyl, $(C_3-C_7)$cycloalkyl$(C_2-C_{12})$alkenyl$(C_3-C_7)$cycloalkyl, $(C_3-C_7)$cycloalkyl$(C_2-C_{12})$alkynyl$(C_3-C_7)$cycloalkyl, $(C_3-C_7)$cycloalkyl$(C_1-C_{12})$alkoxy$(C_3-C_7)$cycloalkyl, $(C_3-C_7)$cycloalkyl$(C_1-C_{12})$alkoxy$(C_1-C_{12})$alkyl $(C_3-C_7)$cycloalkyl, $(C_3-C_7)$cycloalkyl$(C_1-C_{12})$alkoxy $(C_1-C_{12})$alkenyl$(C_3-C_7)$cycloalkyl, $(C_3-C_7)$cycloalkyl $(C_1-C_{12})$alkoxy$(C_1-C_{12})$alkynyl$(C_3-C_7)$cycloalkyl, aryl, aralkyl, aryl$(C_3-C_7)$cycloalkyl, aryl$(C_3-C_7)$ cycloalkyl$(C_3-C_7)$cycloalkyl, $(C_3-C_7)$cycloalkylaryl, aryl$(C_1-C_4)$alkyl$(C_3-C_7)$cycloalkyl, heterocyclic, aryl $(C_1-C_4)$alkylheterocyclic heterocyclic$(C_1-C_4)$alkyl, heterocyclic$(C_3-C_7)$cycloalkyl and $R_1$, $R_2$, $R_3$ and $R_4$ are independently selected from hydrogen, halogen, $(C_1-C_{12})$alkyl, $(C_1-C_{12})$alkoxy, halo$(C_1-C_{12})$alkyl, $(C_2-C_{12})$alkenyl, $(C_2-C_{12})$alkynyl, $(C_3-C_7)$cycloalkyl, cyano, carboxy, $(C_1-C_4)$ alkoxycarbonyl, aryl, and when taken together $R_2$ and $R_3$ form a $(C_3-C_7)$cycloalkyl ring; and its enantiomers and stereoisomers and agronomically acceptable salts, provided that when n=0 or 1 and m=0 then R and $R_1$ are not both hydrogen and when A is N and V is NH and n and m are both zero then R, $R_1$, $R_2$, $R_3$ and $R_4$ are other than 1 to 3 substituents independently selected from halogen and $(C_1-C_4)$alkyl.

2. The compound of claim 1 wherein A is CH.
3. The compound of claim 1 wherein A is N.
4. The compound of claim 3 wherein V is O.
5. The compound of claim 3 wherein V is NH.
6. The compound of claim 1 wherein the moiety

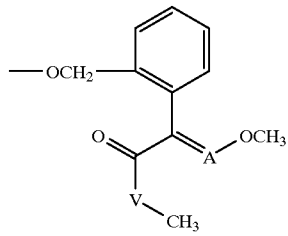

is meta to the substituted cyclopropyl moiety, $R_1$ and $R_4$ are hydrogen and R is selected from the group consisting of $(C_1-C_{12})$alkyl, halo$(C_1-C_{12})$alkyl, heterocyclic, halosubstituted phenyl, $(C_1-C_4)$alkyl substituted phenyl, trihalosubstituted phenyl, $(C_3-C_7)$ cycloalkyl, halo$(C_3-C_7)$cycloalkyl, $(C_3-C_7)$cycloalkyl$(C_1-C_{12})$alkyl, $(C_3-C_7)$cycloalkyl-$(C_2-C_{12})$alkenyl, $(C_1-C_{12})$alkyl$(C_3-C_7)$cycloalkyl and $(C_2-C_{12})$alkenyl$(C_3-C_7)$cycloalkyl.

7. The compound of claim 1 wherein n+m=1.
8. The compound of claim 7 wherein n and m are zero.
9. The compound of claim 8 wherein R is selected from the group consisting of $(C_5-C_{12})$alkyl, 2-halophenyl, 3-halophenyl, 4-halophenyl, 2-$(C_1-C_4)$alkylphenyl, 3-$(C_1-C_4)$alkylphenyl, 4-$(C_1-C_4)$alkylphenyl, cyclopropyl, cyclopropyl$(C_1-C_4)$alkyl, cyclopropyl$(C_2-C_4)$alkenyl, $(C_1-C_4)$alkylcyclopropyl, $(C_2-C_4)$alkenylcyclopropyl, 1-cyclopropylcyclopropyl and 2-cyclopropylcyclopropyl.

10. The compound of claim 9 wherein R is selected from 4-chlorophenyl, 4-flourophenyl, 4-methylphenyl, 2-thienyl, 2-furyl, cyclopropyl and 1-cyclopropyl-1-propenyl.

11. A fungicidal composition for controlling phytopathogenic fungi which comprises an agronomically acceptable carrier and the compound of claim 1 wherein the ratio of the carrier to the compound is 99:1 to 1:4.

12. The composition of claim 11 wherein the ratio of the agronomically acceptable carrier to compound is 10:1 to 1:3.

13. A method for controlling phytopathogenic fungi which comprises applying to the locus where control is desired the compound of claim 1 at a rate of from 0.005 to 50 kilograms per hectare.

14. The method of claim 13 wherein the compound of claim 1 is applied at the rate of from 0.025 to 10 kilograms per hectare.

15. A method for controlling insects which comprises applying to the insect's habitat the compound of claim 1 at a rate of 0.005 to 10 kilograms per hectare.

16. The method of claim 15 wherein the compound is applied at a rate of 0.01 to 1 kilogram per hectare.

* * * * *